United States Patent
Fava et al.

(10) Patent No.: US 9,186,450 B2
(45) Date of Patent: *Nov. 17, 2015

(54) METHOD AND APPARATUS FOR PRIMING AN EXTRACORPOREAL BLOOD CIRCUIT

(71) Applicant: GAMBRO LUNDIA AB, Lund (SE)

(72) Inventors: Massimo Fava, Mirandola (IT); Mauro Suffritti, Medolla (IT); Alessandro Scaglione, Mirandola (IT)

(73) Assignee: Gambro Lundia AB, Lund (SE)

( * ) Notice: Subject to any disclaimer, the term of this patent is extended or adjusted under 35 U.S.C. 154(b) by 362 days.

This patent is subject to a terminal disclaimer.

(21) Appl. No.: 13/964,054

(22) Filed: Aug. 10, 2013

(65) Prior Publication Data

US 2013/0319917 A1 Dec. 5, 2013

Related U.S. Application Data

(63) Continuation of application No. 12/595,038, filed as application No. PCT/IB2007/000944 on Apr. 12, 2007, now Pat. No. 8,529,487.

(51) Int. Cl.
*A61M 1/36* (2006.01)
*A61M 1/30* (2006.01)
(Continued)

(52) U.S. Cl.
CPC ........... *A61M 1/3621* (2013.01); *A61M 1/1627* (2014.02); *A61M 1/1662* (2014.02); *A61M 1/1682* (2014.02); *A61M 1/302* (2014.02); *A61M 1/303* (2014.02); *A61M 1/3465* (2014.02); *A61M 1/365* (2014.02); *A61M 1/3629* (2014.02); *A61M1/3643* (2013.01); *A61M 1/3649* (2014.02); *A61M 1/169* (2013.01); *A61M 1/1656* (2013.01); *A61M 1/1686* (2013.01); *A61M 1/3626* (2013.01); *A61M 2205/3331* (2013.01); *A61M 2205/6018* (2013.01); *A61M 2205/6072* (2013.01)

(58) Field of Classification Search
CPC ........... A61M 1/1627; A61M 1/1656; A61M 1/1662; A61M 1/1682; A61M 1/1686; A61M 1/169; A61M 1/302; A61M 1/303; A61M 1/3465; A61M 1/3621; A61M 1/3626; A61M 1/3629; A61M 1/3643; A61M 1/3649; A61M 1/365; A61M 2205/3331; A61M 2205/6081; A61M 2205/6072

See application file for complete search history.

(56) References Cited

U.S. PATENT DOCUMENTS

| | | | |
|---|---|---|---|
| 4,707,335 A | 11/1987 | Fentress et al. |
| 5,041,215 A | 8/1991 | Chamberlain, Jr. et al. |

(Continued)

FOREIGN PATENT DOCUMENTS

| | | | |
|---|---|---|---|
| DE | 89 04 529 U1 | 5/1989 |
| EP | 0 992 254 A2 | 4/2000 |

(Continued)

*Primary Examiner* — Philip R West
*Assistant Examiner* — Benjamin Klein
(74) *Attorney, Agent, or Firm* — K&L Gates LLP

(57) ABSTRACT

A method and apparatus for priming an extracorporeal blood circuit, in which the patient end of an arterial line (79) is connected to a first discharge port (61), and the patient end of a venous line (87) is connected to a second discharge port (62). The two discharge ports are connected to a used dialysate line which connects a dialyzer (33) to a drain. The arterial and venous lines are filled with a priming fluid, while the air contained in the arterial and venous lines is evacuated partly through the first discharge port and partly through the second discharge port. Two check valves (65, 66) prevent flow from the used dialysate line towards the two discharge ports. The invention reduces the risk of errors on the part of an operator readying the priming configuration, as well as the risk of contamination of the extracorporeal circuit during the priming phase.

24 Claims, 6 Drawing Sheets

(51) Int. Cl.
*A61M 1/34* (2006.01)
*A61M 1/16* (2006.01)

(56) References Cited

U.S. PATENT DOCUMENTS

| | | | |
|---|---|---|---|
| 5,336,165 A | | 8/1994 | Twardowski |
| 5,484,397 A | * | 1/1996 | Twardowski ................ 604/5.01 |
| 5,584,806 A | | 12/1996 | Amano |
| 5,650,071 A | * | 7/1997 | Brugger et al. ............... 210/646 |
| 5,776,091 A | | 7/1998 | Brugger et al. |
| 5,948,251 A | | 9/1999 | Brugger |
| 6,274,034 B1 | | 8/2001 | Nikaido et al. |

FOREIGN PATENT DOCUMENTS

| | | |
|---|---|---|
| WO | 96/40320 A1 | 12/1996 |
| WO | 2005/118485 A1 | 12/2005 |
| WO | 2007/131611 A2 | 11/2007 |

* cited by examiner

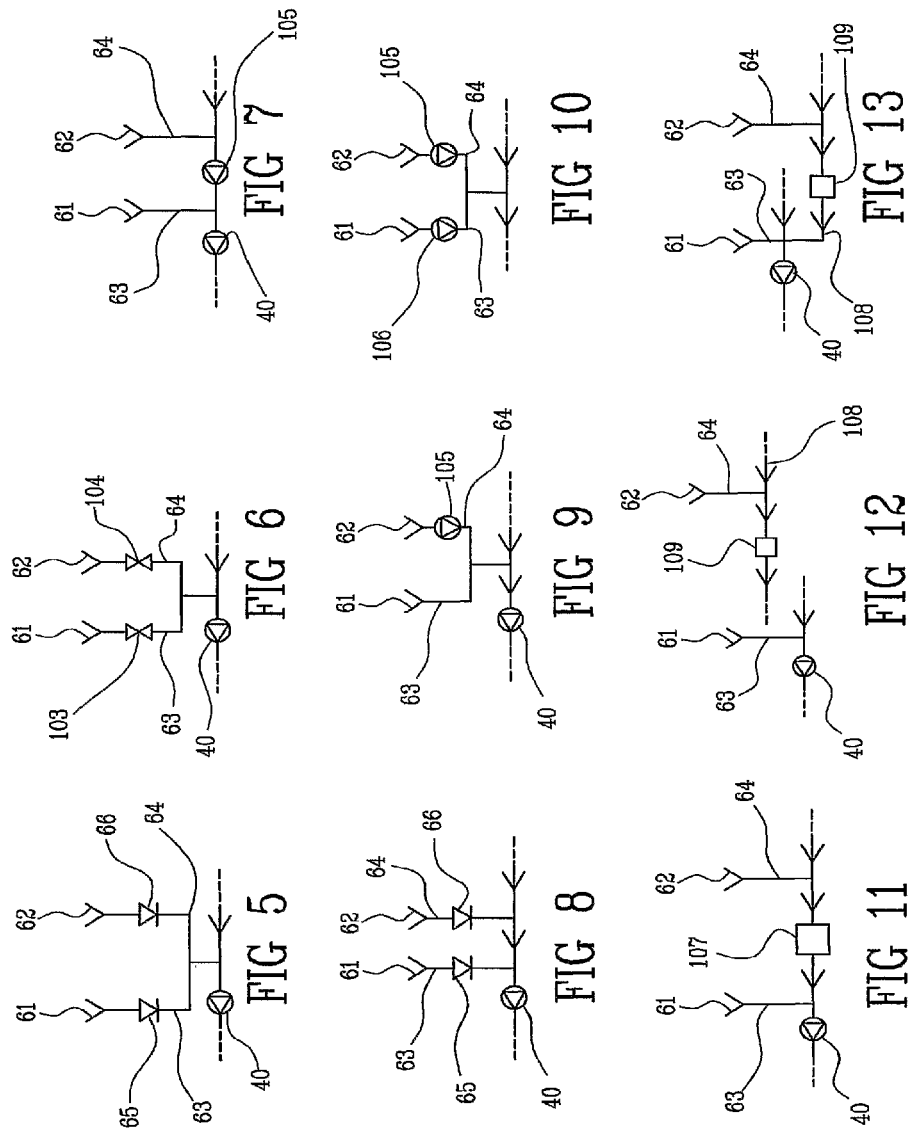

METHOD AND APPARATUS FOR PRIMING AN EXTRACORPOREAL BLOOD CIRCUIT

BACKGROUND OF THE INVENTION

The invention relates to a method and an apparatus for priming an extracorporeal blood circuit.

Specifically, though not exclusively, the invention is usefully applied for priming a dialysis set.

U.S. Pat. No. 4,707,335 describes a system for disinfection and reuse of a membrane separator for blood treatment and fluid transport lines associated to the separator. The system comprises a manifold defining internally a cavity and externally two connectors connected to the patient end of an arterial blood line and a venous blood line, so that the blood lines are intercommunicating with each other, forming a closed fluid circuit in which a disinfecting solution can be made to circulate, for reuse purposes.

U.S. Pat. No. 5,948,251 describes a dialysis machine provided with a disinfection port, a discharge port and a blood pump. Also described is a process for disinfecting a blood tubing set which includes connecting an end of the blood tubing set to the disinfection port and an opposite end thereof the discharge port. The blood tubing set is coupled to the blood pump which pumps the disinfecting solution from the disinfection port to the discharge port.

WO 96/40320 describes a priming method according to which, before the treatment a disposable blood tubing set and a dialyser (new or used) are attached to a dialysis machine and prepared by an operator for use on a patient. The blood tubing set and the dialyser are filled with a sterile saline solution to remove the air from the extracorporeal circuit and to rinse same. To guarantee complete removal of the all traces of undesirable substances from the membrane, the saline solution is recirculated through the dialyser for a predetermined period of time. The recirculating further guarantees that any excess air remaining in the circuit is expelled before connecting the circuit itself to the patient. The blood tubing set comprises a T or Y connector for connecting the two patient ends of the arterial and venous lines to a discharge port connected to a discharge line which is in turn connected to a drainage system. The discharge line can be part of the dialysis machine discharge circuit, i.e. the circuit connecting the outlet of the exhausted dialyser liquid of the dialyser to the drainage system, or can be a line which is separate from the above-cited discharge circuit. The drainage system is the same that receives the used dialysis fluid from the dialysis machine during the treatment. A discharge valve selectively opens or closes the discharge line. The discharge valve can be operated manually or can be controlled by the control unit of the dialysis machine. In the initial priming configuration, an end of the T or Y connector is sealedly coupled with the discharge port, while the other two ends are coupled to the arterial and venous lines. A bag of saline solution is connected to a service line connected to the arterial blood chamber. The venous and arterial lines are closed by respective clamps which can be controlled by the control unit of the dialysis machine. A vent valve in the arterial blood chamber is opened (manually or by means of an automatically-commanded valve) in order to allow the chamber to fill by force of gravity with the saline solution dropping from the bag. When the arterial chamber is full of the saline solution, the vent is closed and the automatic priming process can begin. The arterial clamp is opened for a predetermined time to enable the tract of arterial line comprised between the arterial chamber and the patient arterial end connected to the discharge port to fill with saline solution. Then the arterial clamp is closed, the venous clamp opened, and the blood pump begins to rotate (forward, i.e. in the rotation direction which it normally has during the treatment) in order to fill the rest of the extracorporeal circuit with saline solution from the bag. Once the circuit is filled, the discharge valve is closed, the arterial clamp opened and the blood pump made to rotate backwards (in the opposite direction to its normal direction during treatment) in order to cause the saline solution to circulate through the extracorporeal circuit. During this phase any air left in the blood compartment of the dialyser is transferred into the arterial chamber and remains there in the upper part of the chamber. Thereafter the blood pump is rotated forwards for a further recirculating stage during which the ultrafiltration system of the dialysis machine generates an ultrafiltration flow through the membrane, from the blood compartment to the dialyser compartment of the dialyser in order to guarantee the cleanliness of the membrane. After the patient has been connected to the extracorporeal circuit, the Y or T connector is removed.

One of the drawbacks of the method described in WO 96/40320 is the risk of contamination of the extracorporeal blood circuit by contaminating agents originating from the discharge port, especially in the recirculating stage.

A further drawback consists in the special care and attention the operator must take during the apparatus readying stage of the apparatus in the priming configuration, with a consequent increase in work times, extra work for the operator, the need to have well-trained operators and the risk of error.

SUMMARY OF THE INVENTION

An aim of the present invention is to provide a priming method and an apparatus which obviate the above-described limitations and drawbacks in the prior art.

A further aim of the invention is to reduce the risk of contamination of the extracorporeal blood apparatus during the priming procedure.

An advantage of the invention is that it facilitates the operator's task during the readying stage of the priming configuration, with a reduction in work times and risk of error.

A further advantage is that it avoids a recirculating stage during the priming procedure. This reduces the risk of backflow of air which has been already expelled from the dialyser chamber.

These aims and more besides are all attained by the invention as it is characterised in one or more of the appended claims.

The priming fluid used can be water or a fluid which is isotonic to human blood, for example an isotonic saline solution or a dialysate or a still further liquid.

Moreover we describe herein below a solution to the problem of detachment of the air bubbles internally of the hollow fibres which form the semi-permeable membrane of a dialyser or a hemo(dia)filter during a priming procedure. In particular reference is made to a dialyser or a hemo(dia)filter of a type having a bundle of hollow fibres. In particular the blood chamber of the dialyser or hemo(dia)filter comprises an inside volume of the hollow fibres of a hollow fibre bundle, while the fluid chamber (dialysate chamber and/or filtered fluid chamber) comprises the volume comprised between the external side of the hollow fibres and a casing which closes the hollow fibre bundle. It is known that the process of priming an extracorporeal circuit has the aim of eliminating the air contained in the circuit before connecting the circuit to the patient for the dialysis or hemo(dia)filtration treatment. To guarantee complete detachment of the air bubbles during the priming procedure a method and an apparatus are provided for priming a dialyser or hemo(dia)filter according to a further invention, of which a detailed description is provided herein below. In a first embodiment the priming method comprises the following stages: providing a dialyser or a hemo (dia) filter having a blood chamber defined by the internal volume of the hollow fibres of a bundle of hollow fibres; connecting to the blood chamber at least a blood line; connecting to the blood line at least a blood pump; connecting to the blood chamber a source of a priming fluid; activating the pump in order to displace the priming fluid from the source thereof to the blood chamber, the blood pump being activated intermittently based on two (or three, or more than three) preset values corresponding to different activation velocities of the blood pump, the intermittent action causing variations of speed in the priming fluid flow, in order to detach air bubbles from the internal side of the hollow fibres. The variation of speed in the priming fluid flow causes the detachment of air bubbles from the internal side of the hollow fibres. The variation of speed in the priming fluid flow shall be relatively brusque. Said speed variation shall be sufficiently brusque to cause said air bubble detachment. The sharpness of the speed variation will depend on, inter alia, the type of the hollow fibre bundle. In a second embodiment, the source of priming fluid of the first embodiment can be connected to the blood chamber in order that the blood chamber is arranged between the source of a priming fluid and the blood pump. In further embodiments, the blood pump of the first or the second embodiments can be activated in order to displace the priming fluid from the source thereof to the blood chamber and thereafter from the blood chamber to an inlet of the blood pump. With reference to all of the preceding embodiments, at least one of the above preset values can also correspond to a nil velocity of priming fluid flow. With reference to all of the preceding embodiments, the above-mentioned preset values correspond to displacements of the priming fluid at various speeds (one of which could be a nil velocity) from the source thereof to the blood chamber and thereafter from the blood chamber to an inlet of the blood pump. With reference to all the preceding embodiments, the source of the priming fluid can comprise a container of priming fluid connected to the blood chamber and/or a back-filtration flow which originates in the dialyser or hemo(dia)filter fluid chamber and which flow through the semipermeable membrane. With reference to all of the preceding embodiments, the blood pump can comprise a tube-deforming pump, for example a rotary pump. With reference to all of the preceding embodiments, at least two of said preset values correspond to different or equal activation velocities of the blood pump in the same direction. In a first embodiment thereof the priming apparatus comprises: a dialyser or hemo(dia)filter having a blood chamber defined by the internal volume of the hollow fibres of a bundle of hollow fibres; at least a blood line connected to the blood chamber; at least a blood pump connected to the blood line; at least a source of a priming fluid, connected to the blood chamber; a control unit programmed to activate the blood pump in order to displace the priming fluid from the source of a priming fluid to the blood chamber, the blood pump being activated intermittently, based on two (or three, or more than three) preset values corresponding to different activating velocities of the blood pump, the intermittent activation causing (brusque) variations of velocity of the priming fluid flow, so as to detach air bubbles from the internal side of the hollow fibres. In a second embodiment of the apparatus, the source of a priming fluid of the first embodiment can be connected to the blood chamber in order for the blood chamber to be arranged between the source of a priming fluid and the blood pump. In further embodiments of the priming apparatus, the control unit can be programmed so that the blood pump of the first or second embodiment is activated in order to displace the priming fluid from the source of a priming fluid to the blood chamber, and thereafter from the blood chamber to an inlet of the blood pump. With reference to all the preceding embodiments, at least one of the above-mentioned preset values can also correspond to a nil flow velocity of the priming fluid. With reference to all the preceding embodiments, the above-mentioned values correspond to priming fluid displacements at various speeds (one of which could be nil) from the source of a priming fluid to the blood chamber and, thereafter, from the blood chamber to an inlet of the blood pump. With reference to all the preceding embodiments, the priming fluid source can comprise a container of priming fluid connected to the blood chamber, and/or a back-filtration flow which originates in the dialyser or hemo(dia)filter fluid chamber and which crosses the semipermeable membrane, the apparatus comprising means for back-filtration commanded by the control unit, specially programmed for this purpose. With reference to all the preceding embodiments, the blood pump can comprise a tube-deforming pump, for example a rotary pump. With reference to all of the preceding embodiments, at least two of said preset values correspond to different or equal activation velocities of the blood pump in the same direction of the blood pump. The above-described embodiments, relating to a method and an apparatus, in reference to the further invention which solves the problem of the complete detachment of air bubbles, can all be combined in all the embodiments of method and apparatus which have been and which will be described in the present application, with reference to the first invention, which is directed at resolving the problem of the discharge of the priming fluid.

Further characteristics and advantages of the present invention will better emerge from the detailed description that follows, of various embodiments of the invention, illustrated purely by way of non-limiting example in the accompanying figures of the drawings.

BRIEF DESCRIPTION OF THE DRAWINGS

The description will be made herein below with reference to the accompanying figures of the drawings, provided by way of non-limiting example, in which.

Figure 15:
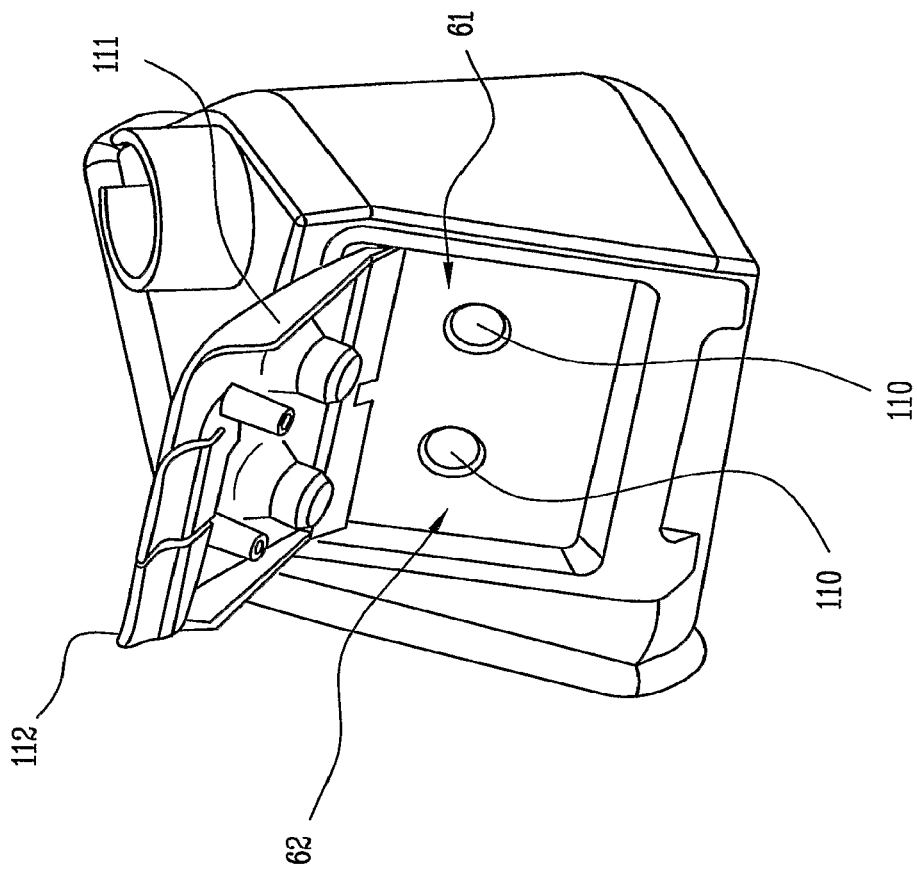
Figure 14:
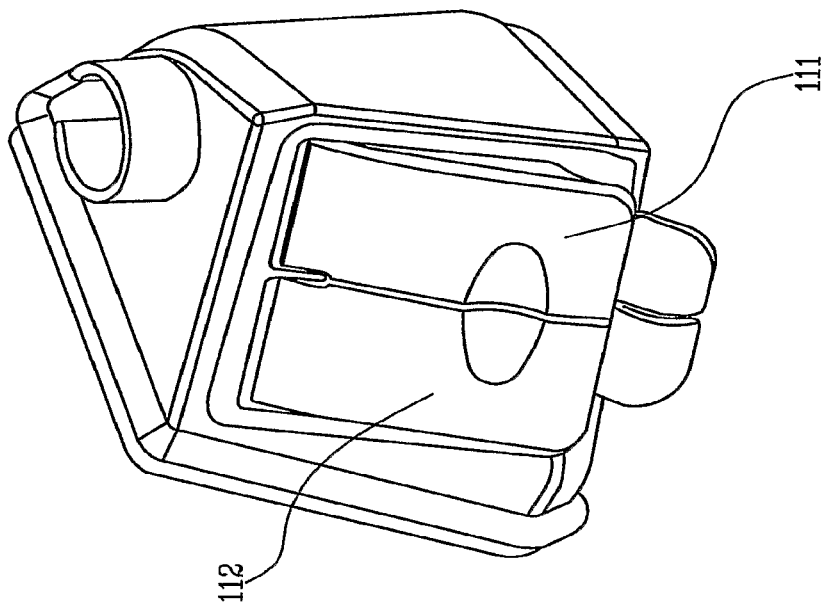

Figures from 5 to 13 are schematic illustrations of some embodiments of the priming apparatus of the invention;

FIGS. 14 and 15 illustrate the two priming fluid discharge ports in a partial view of a front panel of the casing of the priming apparatus.

DETAILED DESCRIPTION

Figure 1:
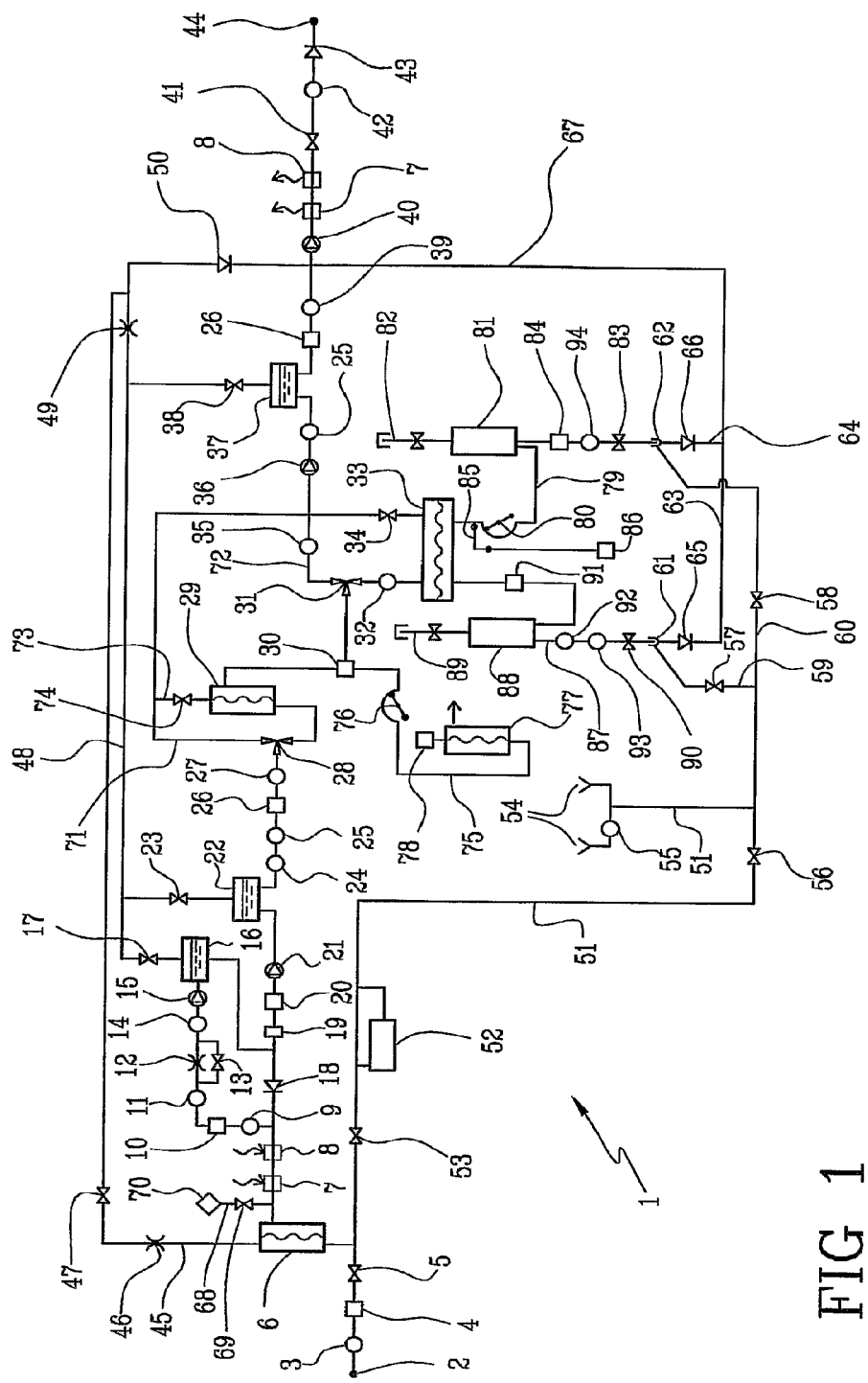
FIG. 1 is a hemodiafiltration apparatus provided with a device for filling and flushing an extracorporeal blood circuit of the invention.

With reference to FIG. 1, 1 denotes in its entirety a hemodiafiltration apparatus, 2 an inlet end connected to a water source, 3 a pressure sensor at the inlet, 4 an inlet pressure regulator, 5 an on-off valve at the inlet, 6 an ultrafilter for the water at the inlet, 7 a first heat exchanger, 8 a second heat exchanger, 9 a flow sensor or a sensor of the presence of a flow (or a flow switch) at the inlet of the heating and degassing circuit, 10 a heater, 11 a temperature sensor in the heating and degassing circuit, 12 a degassing choke or restrictor, 13 a bypass valve of the degassing choke or restrictor, 14 a pressure sensor for controlling the degassing pump, 15 a degassing pump, 16 a first gas-liquid separator in the heating and degassing circuit, 17 a first degassing valve connected to the vent of the first gas-liquid separator, 18 a check or non-return valve for the heating and degassing circuit, 19 a pressure regulator at the outlet of the heating and degassing circuit, 20 a device for on-line preparation of a dialysis fluid with water and concentrates, 21 a pump for moving the fresh dialysis fluid upstream of the dialyser, 22 a second gas-liquid separator for the fresh dialysis fluid, 23 a second degassing valve connected to the vent of the second gas-liquid separator, 24 a sensor system for measuring some parameters (in particular temperature, conductivity and pH) of the fresh dialysate downstream of the second gas-liquid separator, 25 a redundant fluid balance protection system in the control system, 26 a control system for the fluid balance, 27 a pressure sensor at the inlet of the dialysate ultrafilter, 28 a first bypass valve for the bypass of the dialysate ultrafilter, 29 a dialysate ultrafilter, 30 a connection for a disposable substitution fluid line, 31 a second by-pass valve for the dialyser by-pass, 32 a pressure sensor at the dialyser inlet, 33 a dialyser, 34 an on-off valve at the dialyser outlet, 35 a pressure sensor at the dialyser outlet, 36 a pump for moving the used dialyser liquid downstream of the dialyser, 37 a third gas-liquid separator for the used dialysate, 38 a third degassing valve connected to the vent of the third gas-liquid separator, 39 a sensor system for measuring some parameters (in particular temperature, conductivity, pressure and presence of blood leaks) of the used dialysate (downstream of the third gas-liquid separator), 40 a suction pump for stabilizing the pressure downstream of the control system of the fluid balance, 41 a normally-open on-off valve at the outlet, 42 a pressure sensor at the outlet, 43 a check or non-return valve at the outlet, 44 an outlet end connected to a drainage, 45 a flushing line of the water ultrafilter, 46 a choke or restrictor on the flushing line, 47 an on-off valve on the flushing line, 48 a vent circuit connected to the vents of the various gas-liquid separators, 49 a choke or restrictor connected to the vents of the various gas-liquid separators, 50 a check or non-return valve operating on a tract of line in common with the fluid line and the vent circuit, 51 a recirculating circuit for (complete) thermal or chemical disinfection of the circuit, 52 a source of a chemical disinfectant including means for supplying the disinfectant, 53 a first on-off valve to enable recirculation during thermal or chemical disinfection, 54 a pair of connectors for the bypass of the dialyser during the thermal or chemical disinfection, 55 a flow sensor in the dialyser bypass, 56 a second on-off valve for enabling recirculation during the thermal or chemical disinfection, 57 a first on-off valve for enabling supply of the disinfectant to the first discharge port of the priming fluid, 58 a second on-off valve for enabling supply of the disinfectant to the second discharge port of the priming fluid, 59 a first branch for disinfection of the first discharge port of the priming fluid, 60 a second branch for disinfection of the second discharge port of the priming fluid, 61 a first discharge port of the priming fluid, 62 a second discharge port of the priming fluid, 63 a first discharge line of the priming fluid, 64 a second discharge line of the priming fluid, 65 a first check or non-return valve on the first discharge line of the priming fluid, 66 a second check or non-return valve on the second discharge line of the priming fluid, 67 a line joining the first and the second discharge lines of the priming fluid with the used dialysate line, 68 a line connecting into the outside environment upstream of the water heating and degassing circuit, 69 an on-off valve of the environment connection line, 70 an air filter arranged at the inlet of the connection line to the environment, 71 a first dialysate ultrafilter by-pass line, 72 a second dialyser by-pass line, 73 a dialysate ultrafilter flushing line, 74 an on-off valve of the dialysate ultrafilter flushing line, 75 a substitution fluid supply line, 76 a substitution fluid moving pump, 77 a substitution fluid ultrafilter, 78 a vent system of the substitution fluid ultrafilter, 79 an arterial line of an extracorporeal blood circuit, 80 a blood displacement pump, 81 an arterial chamber for gas-liquid separation in the arterial line, 82 a service line of the arterial chamber, 83 an arterial clamp of the arterial line, 84 an access site in the arterial line, 85 an anticoagulant supply line, 86 an anticoagulant source, 87 a venous line of the extracorporeal blood circuit, 88 a venous chamber of gas-liquid separation in the venous line, 89 a service line to the venous chamber, 90 a venous clamp in the venous line, 91 an access site in the venous line, 92 a bubble sensor (air detector) in the venous line, 93 a blood presence sensor (patient sensor), 94 a hemoglobin or hematocrit sensor (blood volume sensor).

The hemodiafiltration apparatus 1 can be used as a hemodialysis apparatus and/or as a hemofiltration apparatus. The water source can be, for example, the municipal water supply or the clinic's water supply. The water source can also be the outlet of a water treatment plant. It is possible to connect the inlet end with a filter, of known type and not illustrated, for preventing inlet of relatively large particles into the hydraulic circuit of the apparatus 1. The pressure sensor 3 is connected to the control unit which is programmed to control the heater 10 according to the signal provided by the pressure sensor 3. In particular the control unit turns off the heater 10 if the pressure at the inlet drops below a predetermined threshold pressure level. The pressure regulator 4 keeps the pressure downstream of the regulator at a constant preset level. This level is preset so that the boiling temperature of the water in the heating circuit is sufficiently high to obtain an effective thermal disinfection. The valve 5 is normally closed and is opened on command of the control unit, in particular when water is to be supplied to the circuit. The valve 69 is normally closed and is opened on command of the control unit, in particular when air is to be introduced into the apparatus 1 hydraulic circuit (for example in a circuit evacuation procedure). The ultrafilter 6 prevents inlet of bacteria or endotoxins. The two heat exchangers 7 and 8 are arranged in series, one after the other. The two exchangers 7 and 8 are configured to exchange heat between a fluid transport line upstream of the dialyser 33 (water or fresh dialysate supply line) and a fluid transport line downstream of the dialyser 33 (used dialysate discharge line). The heater 10 is controlled in feedback by the control unit to heat the water according to the temperature measured by the sensor 11. The sensor 9 is connected to the control unit which is programmed to intervene if the flow across the sensor 9 drops below a predetermined threshold flow level: in particular the control unit is programmed to deactivate the heater 10. The bypass valve 13 of the choke or restrictor 12 is normally closed and is opened on command by the control unit, in particular during the circuit thermal disinfection procedure. The degassing pump 15 is connected to the control unit which is programmed to activate the pump 15 according to the pressure measured by the sensor 14. The pump 15 is a positive displacement pump as, for example, a gear pump. The gas-liquid separator 16 is provided with a liquid level sensor (for example an infrared or ultrasound sensor) of known type and not illustrated. The liquid level sensor is connected to the control unit which is programmed to open the respective degassing valve 17, in order for the air accumulated in the separator chamber 16 to be vented towards the end 44 and therefore discharged in the drain. The device 20 can comprise any known system for the preparation of dialysate starting from water and concentrates. The device 20 comprises the control system and the protection system to guarantee that the dialysate has the desired composition and temperature. In particular the device 20 can comprise the Gambro BICART SELECT® system. In addition or alternatively to the on-line preparation device 20, the apparatus 1 can comprise a system which is predisposed to receive dialysate from an external centralized preparation plant. The pump 21 is connected to the control unit which is programmed to control the pump 21 according to a signal provided by the control system 26 and/or the protection system 25, and/or by the pressure sensor 32. The gas-liquid separator 22 is provided with a liquid level sensor (for example an infrared or ultrasound sensor) of known type and not illustrated. The liquid level sensor is connected to the control unit which is programmed to open the respective degassing valve 23 in order that the air accumulated in the separator chamber 22 is vented towards the end 44 and thereafter discharged into the drainage. The control system 26 can comprise any known fluid balancing system of a hemodialysis or hemo(dia)filtration machine. In particular the control system 26 comprises two flow-meters (for example mass flow-meters, e.g. Coriolis flowmeters), which are arranged one upstream and the other downstream of the dialyser and which are connected to the control unit. The protection system 25 can comprise two flow-meters, in particular of different type to the two flow-meters of the control system 26. In the specific case the two flow-meters of the protection system comprise two volumetric flow-meters, for example two gear flow-meters. The two flow-meters of the protection system 25 are arranged one upstream and the other downstream of the dialyser and are connected to the control unit. The ultrafilter 29 prevents the passage of bacteria or endotoxins towards the dialyser 33. The sensors 27 and 32 and/or 35 are used for determining the trans-membrane pressure of the ultrafilter 29 and for monitoring the state of the ultrafilter. The valve 74 is normally closed and is opened during a tangential washing stage of the ultrafilter 29. A pressure regulator (not illustrated) is arranged between the connection 30 and the bypass valve 31 in order to maintain a predetermined positive pressure at the connection to the substitution liquid line. The valve 31 can be used to configure a hemodialysis (or hemodiafiltration) apparatus or a hemofiltration apparatus. The pump 36 is controlled by the control unit, according to the difference of the flow rates measured by the flow-meter downstream of the dialyser and the flow-meter upstream thereof, in order to obtain a desired flow-rate of patient weight loss and/or ultrafiltration. The gas-liquid separator 37 is provided with a liquid level sensor (for example infrared or ultrasound sensor) of known type and not illustrated. The liquid level sensor is connected to the control unit which is programmed to open the respective degassing valve 38 in order for the air accumulated in the separator chamber 37 to be vented towards the end 44 and thereafter discharged into the drain. The dialyser 33 (or hemofilter or hemodiafilter) is of the hollow fibre bundle type, in which the semipermeable membrane comprises a bundle of hollow fibres. In general the blood chamber is defined as the internal space of the hollow fibres, while the fluid chamber, or dialysis fluid (dialysate) chamber, is defined by the space comprised between the outside of the hollow fibres and a casing which closes the hollow fibre bundle.

The source of the chemical disinfectant 52 may comprise any known chemical disinfection device for a dialysis or hemo(dia)filtration machine. In particular the source can comprise one or more connections for one or more disinfectant containers, one or more pumps for dosing the disinfectant, one or more on-off valves, and at least a flow sensor or a sensor of the presence of flow. The first discharge port 61, as the second discharge port 62, is coupled to a respective patient end of a blood line (arterial and venous) by a connection which comprises a coupling between a tubing set and a drain of the type described in U.S. Pat. No. 5,041,215, which is incorporated herein for reference. It is however possible to use other types of removable connection (for example a luer connector). During the disinfection stage the disinfectant fluid (heated fluid coming from the heater 10, or chemical disinfectant coming from the source 52, or any other type of disinfectant which is usable in a dialysis machine) is supplied selectively to the first port 61, through the first branch 59 with the first valve 57 open and the second valve 58 closed, or to the second port 62, via the second branch 60 with the first valve 57 dosed and the second valve 58 open, in order to guarantee complete filling of the circuit with the disinfectant fluid. The separation chambers 81 and 88, arterial and venous, are connected (in a known way and not illustrated) to a pressure measuring system in the respective chambers, arterial and venous. The measuring system, of known type, can comprise, for each chamber, a device of the type having a deformable membrane, in which the membrane is associated to the chamber and exhibits and internal side in contact with the inside of the chamber and an external side which communicates with a pressure transducer which in turn is connected to the control unit of the apparatus. The measuring system, of known type, can comprise, for each chamber, a service line having a first end connected to the inside of the chamber and a second end connected to the pressure transducer; in general, between the first and second end is located a transducer-protector device of known type.

FIG. 1 shows the hemodiafiltration apparatus in a priming configuration. The priming procedure is done automatically. The operator can, for example, initiate the priming procedure by pressing a start priming button on a user interface of the apparatus. The user interface can comprise, for example, a touch screen. The start-priming button can comprise a touch button. The automatic priming procedure performed by the apparatus 1 comprises the below-described stages, in the paragraph entitled "Priming with back-filtration for a double-needle circuit" with reference to the embodiment of FIG. 2. The apparatus of FIG. 1 can also be used to perform the priming procedure as described below with reference to FIGS. 3 and 4, once the extracorporeal circuit of FIG. 1 has been replaced with the extracorporeal circuits of FIGS. 3 and 4.

Figures from 2 to 4 represent three different embodiments of the priming device of the invention. The embodiments of figures from 2 to 4 comprise some elements that are the same as some elements of the embodiment of FIG. 1, and which have therefore been denoted using the same numbers in the figures. For the description of those elements the description in relation to FIG. 1 is indicated. Further, there are some elements which are common to all three embodiments of figures from 2 to 4 and which are therefore denoted with the same numbers. These elements comprise, in particular, a dialysis apparatus which comprises a dialyser 33, a dialysis fluid circuit, and an extracorporeal blood circuit. The dialyser 33 comprises a blood chamber, a dialysis fluid chamber, and a semipermeable membrane which separates the blood chamber from the dialysis fluid chamber. The dialysis fluid (dialysate) chamber comprises a fresh fluid supply line. The fresh fluid can be, for example, dialysate or isotonic saline solution, or another treatment fluid. The fresh fluid supply line connects a fresh fluid source (for example a dialysate bag or an isotonic saline solution bag, or a device for on-line preparation of dialysate or isotonic saline solution from water and concentrates, or a centralized system for treatment fluid distribution) to an inlet in the dialysate chamber of the dialyser 33. The dialysate circuit further comprises a discharge line for used fluid discharge, which connects an outlet of the dialysate chamber 33 to a drain (for example a collection bag, or the discharge system of the clinic). The dialysate circuit further comprises a by-pass line 72 which bypasses the dialyser 33 connecting the fresh liquid supply line with the used liquid discharge line. The fresh liquid supply line is provided with means for moving the fresh fluid, which in the present embodiment comprise a first pump 21, for example a gear pump or another type of positive-displacement pump. The by-pass line 72 is arranged between the first pump 21 and the dialyser 33. The fresh liquid supply line further comprises a first pressure sensor 32 to detect the pressure of the fresh liquid upstream of the dialyser 33. The by-pass line 72 is provided with a by-pass valve 31, which in the present embodiment comprises a three-way valve which selectively directs the fluid towards the dialyser 33 or the by-pass line 72. The first pressure sensor 32 is arranged between the first pump 21 and the dialyser 33. The dialysate circuit further comprises a second pressure sensor 35 for detecting the fluid pressure downstream of the dialyser 33. In this embodiment the downstream second pressure sensor 35 is situated on the by-pass line 72. The used fluid discharge line is provided with an on-off valve 34. The fluid discharge line used is provided with means for moving the used liquid, which means comprise in the present embodiment a second pump 36, for example a gear pump or another positive displacement pump.

The dialysis apparatus comprises means for ultrafiltration for controlling an ultrafiltration flow which passes through the semipermeable membrane from the blood chamber to the dialysis fluid chamber. The dialysis apparatus further comprises means for back-filtering for controlling a back-filtering flow passing through the semipermeable membrane from the dialysis fluid chamber to the blood chamber. The means for ultrafiltration, like the means for back-filtering, comprise the first pump 21 and the second pump 36 which are activated in a known way to cause a total flow across the membrane in one direction or selectively in the opposite direction. The means for ultrafiltration, in combination with means for control and regulation and with means for measuring, both of known type (not illustrated), form a fluid balancing system for control of a patient's weight loss during a dialysis treatment. The used fluid discharge line comprises, arranged downstream of the second pump 36, means for aspirating, which comprise in the present embodiment a suction pump 40, for example a gear pump or another positive displacement pump. The dialysate circuit comprises a third pressure sensor 95 for detecting the pressure in an intermediate tract of the used liquid discharge line comprised between the liquid balancing system and the means for aspirating; in particular the intermediate tract, in which the third pressure sensor operates 95, is comprised between the second pump 36 and the third suction pump 40.

The dialysate circuit comprises a first branch line or first priming discharge line 63 and a second branch line or second priming discharge line 64, which are connected in branching relation to the intermediate tract of the used liquid discharge line. In the present embodiment each branch line, first and second, branches from the intermediate tract. It is possible, as is the case in FIG. 1, for each branch line to branch from a common tract which branches from the intermediate tract. The first branch line comprises, at a first end thereof, a first connection port, or first priming discharge port 61, for discharging a part of the priming fluid. The first branch line is provided with a first check valve 65 which blocks flow towards the first connection port. The second branch line comprises, at a second end thereof, a second connection port or second priming discharge port 62 for discharging a part of the priming fluid. The second branch line is provided with a second check valve 66 which blocks flow towards the second connection port. The first and the second connection ports are arranged in a zone of the apparatus which is easily accessible from the outside for an operator, for example on a front panel of the apparatus. The first and the second connection ports 61 and 62 are predisposed for sealedly removably connecting with a first and a second end of the extracorporeal blood circuit during the circuit priming stage, as will be more fully explained herein below.

The extracorporeal blood circuit comprises a blood withdrawal line, or arterial line 79, for withdrawing blood to be treated from the patient, and a blood return line, or venous line 87, for return of the treated blood to the patient. The arterial line 79 has a device end which, during the treatment stage (as during the priming phase) is connected to an inlet of the blood chamber of the dialyser 33 (see figures from 2 to 4), and a patient end which is opposite the device end and which, during treatment, is connected to a vascular access device which is in turn connected to the patient's vascular system. Similarly the venous line has a device end which, during the treatment stage (as in the priming stage) is connected to an outlet of the dialyser blood chamber 33 (see figures from 2 to 4), and a patient end which is opposite the device end and which, during the treatment stage, is connected to a vascular access device which is in turn connected to the patient's vascular system. In the illustrated cases in FIGS. 2 to 4, all relating to configurations during a priming stage, the device ends of the arterial and venous lines are connected to the blood chamber of the dialyser, in particular as during the treatment, while the patient ends are connected removably, with a fluid seal, to the first and the second connection ports 61 and 62. In particular, each connection between a patient end and a connection port comprises a coupling between a tubing set and a drain of the type described in U.S. Pat. No. 5,041,215, which is incorporated herewith for reference.

The arterial line 79 further comprises a pump segment which is coupled to a blood pump 80; in the present embodiment the blood pump 80 is of a tube-deforming rotary type (peristaltic), and the pump segment is a tract of deformable tube (squeezable), conformed in an open ring-shape. The arterial line 79 further comprises a squeezable tract which is coupled during operation to an automatic arterial clamp 83, controlled by the control and command unit of the dialysis apparatus. The arterial line 79 further comprises an arterial chamber 81 for gas-liquid separation, provided with a measuring device of the arterial pressure 96. In the illustrated embodiment the measuring device 96 comprises a deformable membrane which is operatively associated, in a known way which is not illustrated, to an arterial pressure sensor connected to the control and command unit. The arterial clamp 83 is arranged between the arterial chamber 81 and the patient arterial end.

The venous line 87 comprises a squeezable tract which is operatively coupled to an automatic venous clamp 90, controlled by the control and command unit of the apparatus. The venous line 87 further comprises a venous chamber 88 for gas-liquid separation provided with a measuring device of the venous pressure 97. In the present embodiment the measuring device 97 comprises a deformable membrane which is operatively associated, in a known way which is not illustrated, to a venous pressure sensor connected to the control and command unit. The venous claim 90 is arranged between the venous chamber 88 and the patient venous end.

Before the dialysis treatment, in particular before connecting the patient to the extracorporeal blood circuit, both the dialyser 33 and the extracorporeal blood lines, both the arterial line 79 and the venous line 87, are full of air which must be expelled. For this purpose a priming process is performed, which consists in filling and flushing or rinsing the dialyser 33 and the blood lines 79 and 87 with a priming fluid, normally constituted by an isotonic liquid (for example saline or dialysis fluid). In the cases of the embodiments in FIGS. 2 and 3, the priming fluid for the blood chamber of the dialyser and for the arterial and venous blood lines is provided by a back-filtering flow through the semipermeable membrane of the dialyser 33 from the dialysate chamber to the blood chamber. In these cases the priming fluid (for example a saline solution or a dialysate) can be prepared on-line by the dialysis apparatus, starting from water and concentrates. In the case of the embodiment of FIG. 4, however, the priming fluid for the blood chamber of the dialyser and for the arterial and venous blood lines is provided by a container 98 of a predefined volume (for example a bag having flexible walls) connected, by a removal connection 99, to the extracorporeal circuit, in particular the venous line. In this embodiment the container 98 is connected to a tract of venous line 87 comprised between the venous clamp 90 and the device end connected to the dialyser 33. In particular the container 98 is connected to the venous chamber 88, for example by means of the service line 89. In this case the service line 89 exhibits a connector (for example a luer connector or another removable coupling) which is coupled to a counter-connector associated to the container 98 in order to achieve the connection 99. In a further version, not illustrated, an auxiliary line can be provided which branches off, for example by means of a Y or a T connection, from the venous line 87, for example from the tract of venous line comprised between the venous chamber 88 and the device end connected to the dialyser 33; this auxiliary line exhibits an end which is provided with a connector for removable connection with the counter-connector associated to the container 98.

Figure 3:
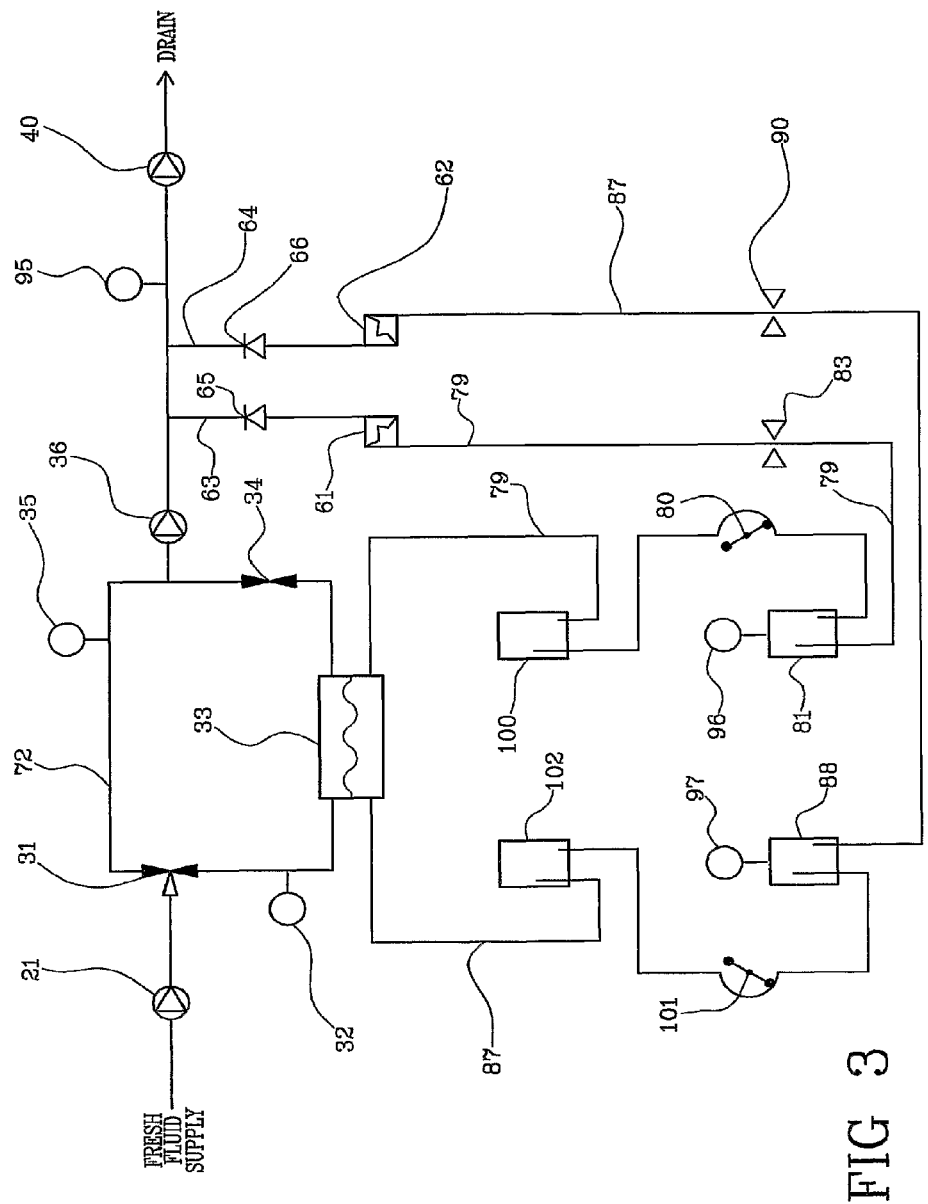
FIG. 3 is a third embodiment of the device for filling and flushing an extracorporeal blood circuit of the invention.

FIG. 3 illustrates a priming apparatus for a single-needle dialysis circuit. The arterial line 79 comprises a second chamber 100 for blood storage arranged between the blood pump 80 and the arterial device end connected to the inlet of the dialyser blood chamber 33. The second arterial chamber 100 is connected to a pressure sensor (not illustrated), for example an identical sensor to the sensor 96 of the first arterial chamber 81. The venous line 87 is connected to a second venous blood pump 101, for example a rotary tube-deforming pump. The second blood pump 101 is operatively associable to a tract of venous line which is conformed as an open ring and configured for coupling to a blood pump. The venous line 87 further comprises a second chamber 102 for blood storage which is arranged between the second blood pump 101 and the venous blood end connected to the outlet of the dialyser blood chamber 33. The second venous chamber 102 is connected to a pressure sensor (not illustrated), for example a sensor which is identical to the sensor 97 of the first venous chamber 88.

Priming with Back-Filtration for a Double-Needle Circuit

The priming process will now be described in greater detail with reference to FIG. 2, which shows the apparatus in the priming configuration.

Phase 1 (set-up)—The arterial and venous blood chambers 81 and 88 are loaded onto the front panel of the dialysis apparatus. The arterial blood line is coupled to the blood pump 80. The device ends of the arterial and venous blood lines are coupled to the blood chamber of the dialyser 33 as during treatment (normally the device arterial end is connected to the upper connection while the device venous end is connected to the lower connection). The patient ends of the arterial and venous blood lines are each coupled to one of the two priming fluid discharge ports 61 and 62 (see FIG. 2); note that a patient end can be coupled to any discharge port; in other words it is not important to which discharge port, the first 61 or second 62, the arterial or venous patient end is connected. The arterial line is coupled to the arterial clamp 83. The venous line is coupled to the venous clamp 90. The venous clamp is closed. The dialysis fluid chamber of the dialyser is connected to the dialysis fluid circuit as during dialysis treatment (see FIG. 2). The rated or nominal value of permeability of the dialyser 33 membrane is entered into the control and command unit of the dialysis apparatus, for example by dialyser recognition via an automatic reader.

Phase 2 (start of the procedure, with removal or air from the dialysis chamber of the dialyser)—This stage is started when the dialysate (or other priming fluid) is ready to be transferred to the dialyser. The priming fluid can be dialysate or isotonic saline solution, prepared on-line by the dialysis apparatus from water and concentrates; in the following, for reasons of simplicity, reference will be made to dialysate used as priming fluid, without losing the general meaning. In the present embodiment, in which the dialysate is prepared on-line by the dialysis apparatus, the dialysate is ready for the dialyser if the temperature and the conductivity are within a predetermined range of acceptability. When the dialysate is ready, the venous clamp 90 is opened. The arterial clamp 83 remains open. The blood pump 80 remains stationery. The on-off valve 34 on the used dialysate discharge line at the outlet of the dialyser is opened. The by-pass valve 31 is activated to close the by-pass line 72 and to enable the flow towards the dialyser 33. The suction pump 40 is controlled in order to maintain a certain pressure in the extracorporeal blood circuit. In particular the suction pump 40 is kept under feedback control at a predetermined pressure by the third pressure sensor 95. Alternatively, or additionally, the suction pump 40 could be controlled by the arterial pressure sensor 96 and/or the venous pressure sensor 97. The means for back-filtering are controlled in order to determine a nil or low back-filtration flow across the dialyser membrane 33 from the dialysate chamber to the blood chamber. During this phase the flow of dialysate crosses the dialysate chamber from the inlet to the outlet (in particular from bottom-to-top placing the dialyser in the use position during treatment) in order to fill and tangentially flush or rinse the dialysate chamber. During this stage the air contained in the dialysate chamber is evacuated through the used (dialysis) fluid discharge line and thus is discharged into the drain. In the present embodiment the first pump 21 of the fresh liquid is controlled at a set flow, for example by the use of a flow sensor providing a feedback signal (as already described previously in relation to the example of FIG. 1). The second pump 36 of the used dialysate is controlled according to the TMP trans-membrane pressure of the dialyser, for example with the aim of obtaining a TMP pressure of zero, so that the back-filtering flow is about zero. The TMP trans-membrane pressure is calculated in a known way, for example by the use of pressure signals provided by the upstream sensor 32, the downstream sensor 35, and the venous sensor 97 (and possibly by a further arterial sensor, not illustrated and arranged between the blood pump 80 and the dialyser 33). Other types of control of the first pump 21 and the second pump (means for back-filtering) are however possible, in which both pumps are controlled by two signals indicating the respective flows, or by a signal indicating the difference of the two flows, or in which both pumps are controlled according to the TMP trans-membrane pressure, and so on. This stage terminates when an air bubble sensor (of known type and not illustrated) predisposed on the used dialysate discharge line detects no further air bubbles, or after a predetermined time-out.

Phase 3 (removal of air from the blood chamber of the dialyser, the arterial line, and part of the venous line)—During this stage the venous clamp 90 remains open. The arterial clamp 83 remains open. The on-off valve 34 of the used dialysate at the outlet of the dialyser 33 remains open. The by-pass valve 31 of the dialyser remains in the closed by-pass position, in which the dialysate is supplied to the dialyser 33. The suction pump 40 is controlled at a set pressure, for example according to the pressure measured by the third pressure sensor 95, or the arterial pressure measured by the arterial sensor 96, or the venous pressure measured by the venous sensor 97. The means for back-filtering are controlled in such a way as to obtain a back-filtration flow which is greater than zero. In the present embodiment the first pump 21 is feedback-controlled by a flow sensor for obtaining a predetermined flow rate for the dialysate upstream of the dialyser. The second pump 36 is feedback-controlled at a predetermined TMP trans-membrane pressure value, so as to generate a back-filtration flow of BFF=Kuf*TMP, where Kuf is the permeability of the dialyser 33 membrane. The blood pump 80 is controlled in the reverse direction (clockwise with reference to FIG. 2), i.e. from the dialyser to the patient arterial end, i.e. in an opposite direction with respect to the rotation direction during the treatment. The blood pump 80 is controlled according to a predetermined sequence. An example of a sequence is provided in the following table.

| Phase | Blood pump flow rate | Time (sec) |
|---|---|---|
| 1 | 0.75 * BFF | 15 |
| 2 | 0.25 * BFF | 30 |
| 3 | 0.50 * BFF | 30 |
| 4 | 0.25 * BFF | 30 |
| 5 | 0 | 20 |
| 6 | 0.75 * BFF | 30 |
| 7 | 0.50 * BFF | 10 |

The flows of the blood pump at each stage are less than the total back-filtration flow BFF, in order to prevent a reverse flow from the venous line 87 towards the blood chamber of the dialyser 33 (note that the check valve 66 is a further safety for preventing the reverse flow). Each change of velocity of the blood pump (from phase 1 to phase 2, from 2 to 3 and so on) is realised in a relatively brief time period, for example a time comprised between 2 and 20 tenths of a second, or in less than a second, with the aim of facilitating the detachment of air bubbles from the blood side of the dialyser membrane, by effect of the shock caused by the sharp flow change. The preset velocity rates of the blood pump can be different from those reported in the example, while still obtaining the effect of detaching the air bubbles attached to the blood side of the dialyser 33 membrane, i.e. in the present embodiment the internal wall of the hollow fibres.

Phase 4 (generation of a negative pressure in the arterial and venous blood chambers by means of the suction pump in order to raise the liquid level)—During this phase the venous clamp 90 remains open. The arterial clamp 83 remains open. The on-off valve 34 downstream of the dialyser remains open. The by-pass valve 31 remains in the by-pass closed position with the dialyser supplied. The blood pump 80 is stationery or is controlled in reverse direction (clockwise) at a predetermined speed. The means for back-filtering are controlled in such a way as to determine a substantially nil back-filtering flow. In particular the first pump 21 is controlled at a predetermined flow rate. The second pump 36 is controlled at a predetermined rate (substantially nil) of trans-membrane pressure TMP. The suction pump 40 is controlled according to one or more pressure values, for example the value measured by the third pressure sensor 95, and/or the value measured by the arterial pressure sensor 96, and/or the value measured by the venous pressure sensor 97, with the aim of transferring gas (air) from the blood circuit, with the effect of raising the liquid levels in the arterial 81 and venous 88 separation chambers. This phase is stopped when a predetermined pressure level is reached in the extracorporeal circuit (for example after four or five seconds). In particular this phase is stopped when the arterial pressure (measured by the sensor 96) and/or the venous pressure (measured by the sensor 97) have reached or exceeded a predetermined value (e.g. a negative value, like −300 mmHg).

Phase 5 (stabilization stage: after raising the levels the negative pressure is gradually increased)—The venous clamp 90, the arterial clamp 83, and the on-off valve 34 at the dialyser outlet are left open. The by-pass valve 31 is left in the by-pass closed position. The blood pump 80 is left stationary or is controlled in the reverse direction (clockwise) at a predetermined velocity. The means for back-filtering are controlled in order to generate a back-filtering flow which is greater than the flow generated by the blood pump 80, so as to prevent a flow (in particular an air-flow) from the venous line 87 to the dialyser 33 blood chamber. In the present embodiment the first pump 21 is controlled according to a prefixed fresh dialysate flow, while the second pump 36 is controlled in such a way as to generate a trans-membrane pressure TMP having a predetermined value. This TMP value is determined (calculated) on the basis of the Kuf permeability (known at the outset or calculable in situ) of the dialyser 33 membrane, so that the back-filtering flow BFF=Kuf*TMP is greater than the flow of the blood pump 80. The suction pump 40 is controlled so as to maintain a predetermined negative pressure in the extracorporeal blood circuit; in particular the suction pump 40 can be feedback-controlled by the third pressure sensor 95 and/or the arterial pressure sensor 96 and/or by the venous pressure sensor 97. This phase terminates after a certain time-out (for example 20 seconds) or after the pressure in the extra-corporeal circuit has been remained at the predetermined value or thereabout for a predetermined time period (for example 20 seconds). During this phase the levels in the separation chambers 81 and 88 are stabilized.

Phase 6 (further detachment of air bubbles from the blood side of the dialyser membrane)—The venous clamp 90, the arterial clamp 83 and the on-off valve 34 at the outlet of the dialyser are left open. The by-pass valve 31 is left in the bypass-closed position and supply towards the dialyser 33 open. The suction pump 40 is controlled at a predefined pressure value, in particular at a value measured by the third pressure sensor 95, and/or the arterial pressure sensor 96, and/or the venous pressure sensor 97. The means for back-filtering are controlled in such a way as to determine a relatively-high (e.g. TMP=−600 mmHg) negative trans-membrane pressure TMP (i.e. such as to generate a back-filtering flow in the direction going from the dialysate chamber to the blood chamber). In particular the first pump 21 is controlled at a predetermined constant flow, while the second pump 36 is controlled according to the desired trans-membrane pressure TMP. The trans-membrane pressure TMP is correlated to a determined back-filtering flow BFF=Kuf*TMP, where Kuf can be, as already mentioned, predetermined and known after dialyser recognition (e.g. by an automatic reader or by the operator which enters the dialyser data), or determined in situ from a trans-membrane pressure and a corresponding known flow (e.g. measured by the fluid balancing system of the dialysis apparatus) of ultrafiltration or back-filtration. The blood pump 80 is controlled on the basis of a predetermined sequence, as indicated for example in the following table.

| Phase | Blood pump flow | Time (sec) |
|---|---|---|
| 5.1 | 0.25 * BFF | 40 |
| 5.3 | 0.75 * BFF | 40 |
| 5.4 | 0.25 * BFF | 10 |

In this case too the blood pump flow represents a fraction of the total back-filtration flow BFF.

Phase 7 (repetition of phase 4, in which the prefixed value to be reached in the extracorporeal circuit at the termination of the phase is lower than in phase 4)—During this phase the venous clamp 90 remains open, the arterial clamp 83 remains open, the on-off valve 34 downstream of the dialyser remains open, the by-pass valve 31 remains in the by-pass-closed position, the blood pump 80 is stationery or is controlled in reverse direction (clockwise) at a predetermined velocity. The means for back-filtration are controlled in such a way as to determine a back-filtering flow which is substantially nil. In particular the first pump 21 is controlled at a predetermined flow rate, while the second pump 36 is controlled at a predetermined value (substantially nil) of trans-membrane pressure TMP. The suction pump 40 is controlled according to one or more pressure values, for example the value measured by the third pressure sensor 95, and/or the value measured by the arterial pressure sensor 96, and/or the value measure by the venous pressure sensor 97, with the aim of transferring (sucking) gas (air) from the blood circuit, with the effect of raising the liquid levels in the arterial 81 and venous 88 separation chambers. This phase is stopped when a predetermined pressure level is reached in the extracorporeal circuit (for example after four or five seconds). In particular this phase is stopped when the arterial pressure (measured by the sensor 96) and/or the venous pressure (measured by the sensor 97) have reached or exceeded a predetermined level (e.g. TMP=−450 mmHg) which is higher than that of phase 4.

Phase 8 (stabilization of the levels in both the separation chambers, arterial and venous)—This phase comprises two sub-phases. In a first sub-phase, the venous clamp 90 remains open, the arterial clamp 83 remains open, the on-off valve 34 downstream of the dialyser remains open, the by-pass valve 31 remains in the closed by-pass position. The blood pump 80 runs in reverse direction (clockwise) at a prefixed velocity in order to generate a certain flow. The suction pump 40 is feedback-controlled at a predetermined pressure (for example measured by the third pressure sensor 95). The means for back-filtering are controlled in such a way as to generate a prefixed negative trans-membrane TMP pressure (for example −600 mmHg) in order to ensure a back-filtering flow which is greater than the flow of the blood pump 80. This first sub-phase terminates after a prefixed timeout (for example 30 seconds). The second sub-phase differs from the first for the fact that the means for back-filtering are controlled in such a way as to determine a trans-membrane pressure TMP which is less than that of the first sub-phase (for example −450 mmHg). The blood pump 80 runs in the reverse direction in order to generate a lower flow-rate than the back-filtering flow. The second sub-phase terminates after a prefixed timeout (for example 20 seconds).

Phase 9 (the dialysate levels in the chambers are now stabilized and the apparatus is ready for connection to the patient)—At the termination of the above second sub-phase the venous clamp 90 is closed, the arterial clamp 83 is closed and the blood pump 80 is stopped. The dialysis monitor controls that there is neither flow nor back-filtration, nor ultrafiltration flow. For example the dialysis monitor can verify that the trans-membrane pressure TMP is about zero (TMP≈0 mmHg). The dialysis monitor controls that the pressure downstream of the dialyser, measured by the second sensor 35 is about zero. The dialysis monitor checks that the pressure in the blood circuit, measured by the arterial pressure sensor 96 and/or the venous pressure sensor 97 is about zero. Following these checks, the priming procedure is terminated and the extracorporeal blood can be connected to the patient in a known way.

Priming with Back-Filtering for a Single Needle Circuit

Figure 2:
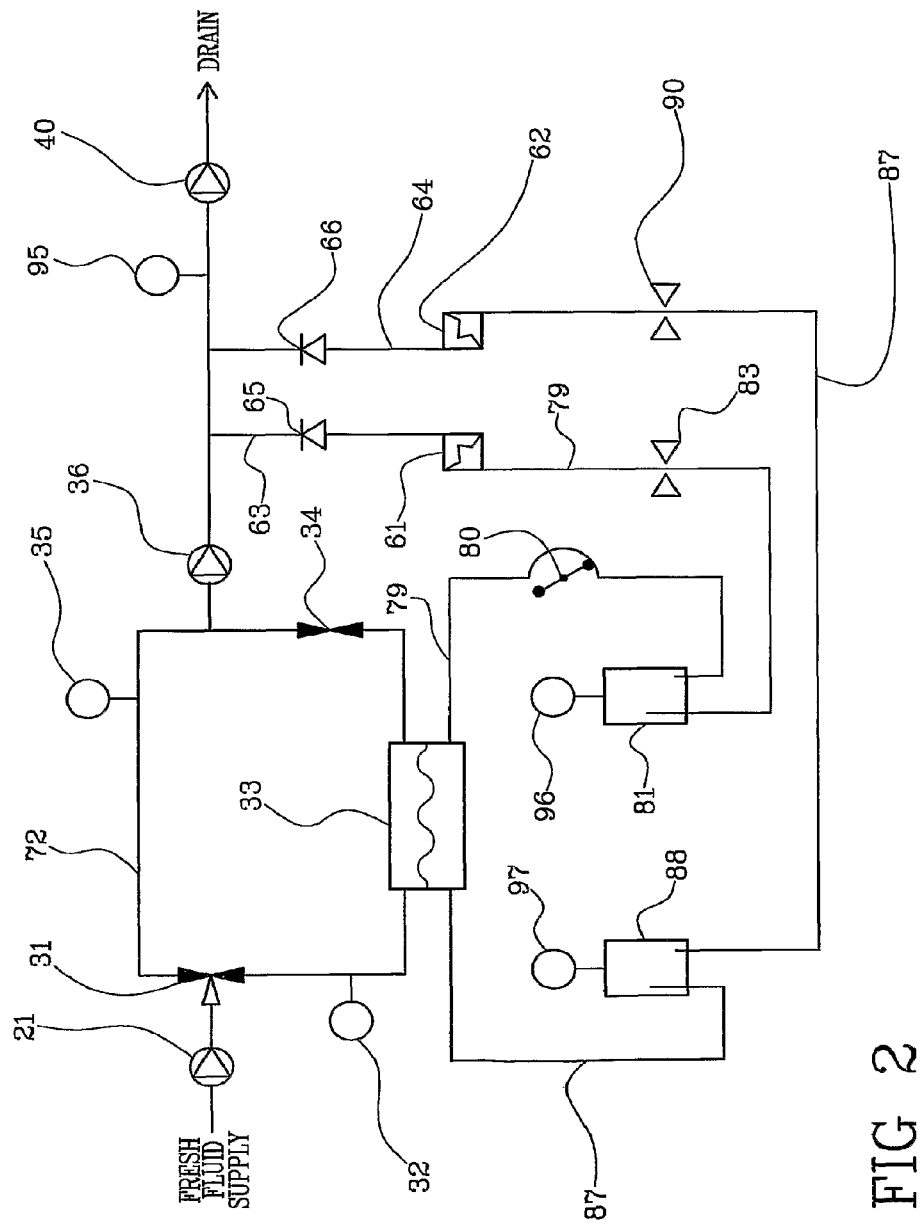
FIG. 2 is a second embodiment of the device for filling and flushing an extracorporeal blood circuit of the invention.

In this case (illustrated in FIG. 3) the dialyser and the dialysate circuit are as in the example of FIG. 2. It is alternatively and equally possible in this case to use the circuit of FIG. 1. The extracorporeal blood circuit comprises, in addition to what is described with reference to FIG. 2 (or FIG. 1), a second arterial chamber for gas-liquid separation, a second venous chamber for gas-liquid separation, a second blood pump arranged on the venous line. The second arterial chamber is arranged between the first blood pump (arterial) and the dialyser. The second venous chamber is arranged between the first venous chamber and the dialyser. The second blood pump (venous) is arranged between the first venous chamber and the second venous chamber. FIG. 3 shows the circuit in the priming configuration.

The priming procedure of the circuit of FIG. 3 is now described.

Phase 1 (set-up)—The four separation chambers are mounted on the front panel of the dialysis apparatus. The arterial and venous lines are coupled to the respective blood pumps and connected to the dialyser as during treatment. The patient ends of the arterial line and the venous line are connected to the first and the second priming fluid discharge ports. The arterial and venous lines are coupled to the respective arterial and venous clamps. The venous clamp is closed. The dialysate chamber of the dialyser is connected to the dialysate circuit as during the treatment.

Phase 2 (evacuation of air from the dialysate chamber)—The procedure will begin when the dialysate (or the isotonic saline solution) are ready. For this purpose, the dialysis monitor checks that the temperature and the conductivity of the dialysate are suitable. Once this check has been carried out, the venous clamp is opened and remains open, the arterial claim remains open, the valve downstream of the dialyser is opened. The by-pass valve closes the by-pass and opens the flow of dialysate towards the dialyser. The two blood pumps remain stationery. The first pump and the second pump cause a tangential flow of dialysate, from the inlet to the outlet of the dialysate chamber, to expel the air contained in the dialysis chamber and to fill and flush the chamber with the dialysate. The air and the dialysate in excess are discharged towards the drain. In particular the first pump is controlled at a constant predetermined flow, while the second pump is controlled at a trans-membrane pressure TMP of about zero in order to have a nil flow through the membrane. The suction pump is controlled at a predetermined pressure, for example arterial pressure or venous pressure, or the pressure at the third sensor. This phase is terminated when the air bubble sensor no longer detects presence of air in the dialysate circuit downstream of the dialyser, or after a predetermined time-out.

Phase 3 (removal of air from the blood chamber)—The venous clamp remains open, the arterial clamp remains open, the valve downstream of the dialyser remains open, the by-pass valve remains in the by-pass closed position. The suction pump is controlled at a predetermined pressure value in the extracorporeal circuit. The first pump is controlled at a predetermined flow value. The second pump is controlled at a predetermined trans-membrane pressure TMP value so as to generate a back-filtering flow BFF=TMP*Kuf. The venous blood pump may be controlled (in anticlockwise direction in FIG. 3) at variable flow-rates in a predetermined sequence. The arterial blood pump is controlled (in clockwise direction in FIG. 3) at variable flow-rates according to a predetermined sequence. A table representing the above-described sequences is included below.

| Phase | Arterial blood pump speed | Venous blood pump speed | Time (sec) |
| --- | --- | --- | --- |
| 1 | 0.25 * BFF | 0.25 BFF | 40 |
| 2 | 0.25 * BFF | 0.5 BFF | 45 |
| 3 | 0.5 * BFF | 0.5 BFF | 40 |
| 4 | 0.75 * BFF | 0.25 BFF | 45 |

Phase 4 (determination of the liquid levels in the various separation chambers)—The venous clamp remains open, the arterial clamp remains open, the on-off valve downstream of the dialyser remains open, the by-pass valve remains in the by-pass closed position. The suction pump is controlled at a predetermined pressure value in the extracorporeal circuit. The first pump is controlled at a predetermined flow rate value. The second pump is controlled at a prefixed trans-membrane pressure TMP value. The venous blood pump rotates in anticlockwise direction and the arterial blood pump rotates in a clockwise direction, both with the aim of aspirating fluid from the dialyser blood chamber. The blood pumps, both arterial and venous, and the suction pump can be controlled, for example, according to the following sequence.

| Phase | Arterial blood pump BP speed (ml/min) | Venous blood pump BP2 speed (ml/min) | Suction pump Pw pressure (mmHg) | Time (sec) |
| --- | --- | --- | --- | --- |
| 1 | 150 | 50 | −400 | 30 |
| 2 | 100 | 100 | −300 | 10 |
| 3 | 100 | 100 | −200 | 10 |
| 4 | 150 | 50 | −100 | 10 |
| 5 | 150 | 50 | −10 | 30 |
| 6 | 100 | 100 | −10 | 30 |
| 7 | 150 | 50 | −400 | 30 |
| 8 | 50 | 150 | −300 | 10 |
| 9 | 50 | 150 | −200 | 10 |
| 10 | 50 | 150 | −100 | 10 |
| 11 | 50 | 150 | −10 | 30 |

Phase 5 (stabilization of the pressures in the separation chambers)—The venous clamp remains open, the arterial clamp is closed, the valve downstream of the dialyser remains open, the by-pass valve remains in the by-pass closed position. The suction pump is controlled at a predetermined pressure value in the extracorporeal circuit. The first pump is controlled at a predetermined flow rate. The second pump is controlled at a predetermined trans-membrane pressure TMP. The venous pump and the arterial pump are stopped. This phase lasts for a determined time period (for example 30 seconds).

Phase 6 (end of the procedure)—The venous clamp is closed, the arterial clamp remains closed, the valve downstream of the dialyser is open, the by-pass valve remains in the by-pass closed position. The suction pump is controlled at a predetermined pressure value in the extracorporeal circuit. The first pump is controlled at a predetermined flow rate level. The second pump is controlled at a predetermined trans-membrane pressure value or range in order to have a nil flow through the membrane BFF=0. The venous pump and the arterial pump remain stationery. This phase lasts for a predetermined time (for example 5 seconds), after which the circuit is connected up to the patient.

In both above-described cases, before starting the priming procedure, the control unit of the dialysis apparatus acquires the permeability value Kuf of the membrane filter membrane (dialyser), for example by recognizing the dialyser (for example by an identifying code associated to the dialyser and recognized by an automatic reader), or by an automatic procedure of determination of said permeability index, for example after the dialyser has been coupled to the hydraulic circuit, by measuring the ultrafiltration flow rate and the corresponding trans-membrane pressure and the following calculation (in a known way) of the Kuf permeability.

In both above-described cases, during the priming procedure the following occurs: the blood pump is controlled at a set flow rate; the first upstream pump P1 is controlled at a set flow rate; the second downstream pump P2 is controlled at a desired pressure (in particular a trans-membrane pressure); the suction pump Pw is controlled at a desired pressure (in particular a pressure upstream of the suction pump); the by-pass valve is passed from the by-pass open position into the by-pass closed position at the start of the procedure and before starting the back-filtering flow; the on-off valve downstream of the dialyser by-pass is opened at the start of the procedure and before the back-filtering flow is initiated.

Priming with Priming Fluid Coming from a Bag

Figure 4:
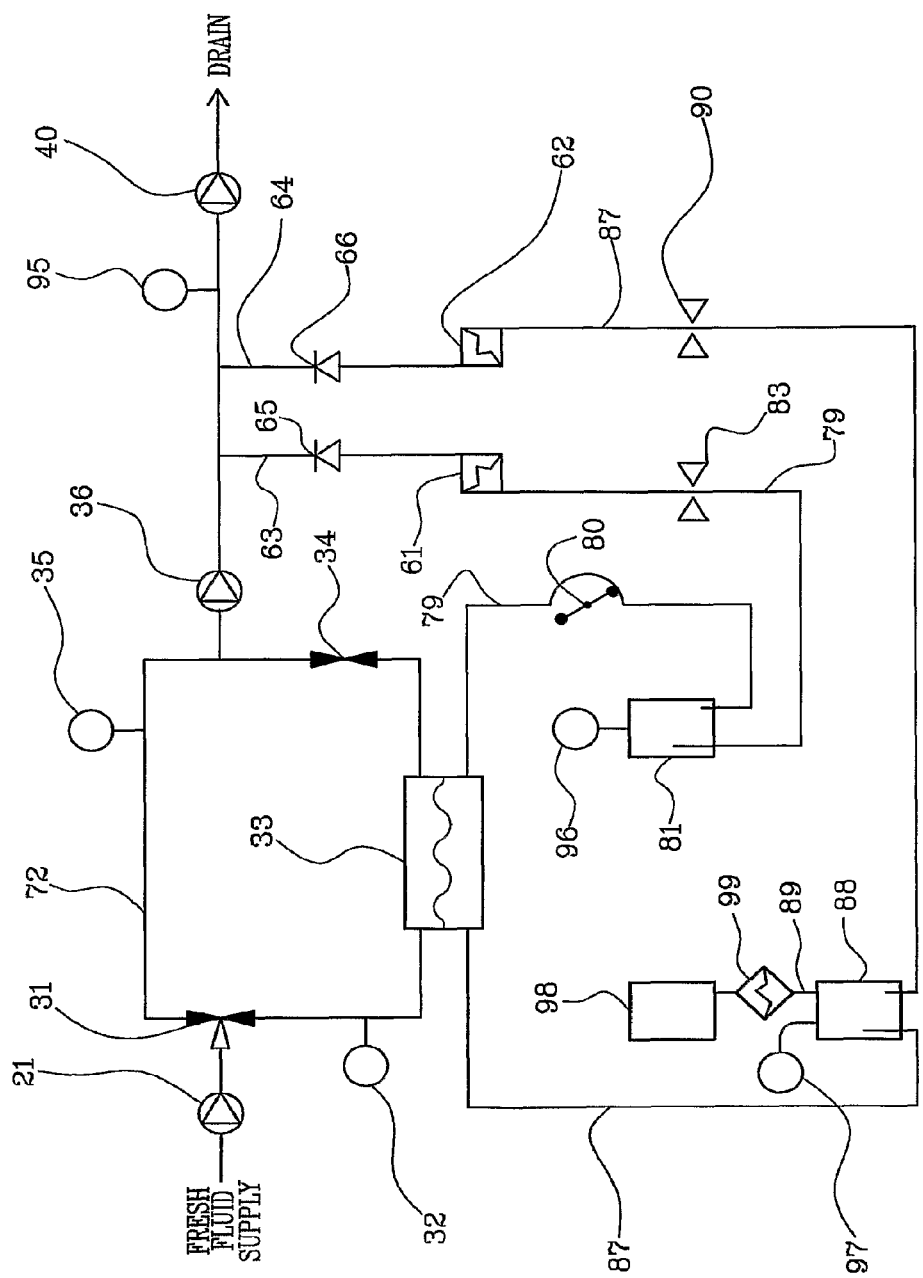
FIG. 4 is a fourth embodiment of the device for filling and flushing an extracorporeal blood circuit of the invention.

There now follows a more detailed description of the priming method with reference to FIG. 4, which shows the apparatus in the priming configuration. FIG. 4 relates to an apparatus for double-needle dialysis. However the procedure is applicable also to an apparatus for single-needle dialysis.

Phase 1 (set-up)—The arterial and venous blood chambers are loaded on the front panel of the dialysis apparatus. The arterial blood line is coupled to the blood pump. The device ends of the arterial and venous blood lines are coupled to the blood chamber of the dialyser as in the treatment (normally the arterial device end is connected to the upper socket while the venous device end is connected to the lower socket). The patient ends of the arterial and venous blood lines are each coupled to one of the two priming fluid discharge ports; note that in the present case a patient end can be coupled to any discharge port; in other words it is not important which discharge port, the first or second, a determined patient end is coupled to, it can be either arterial or venous. The arterial line is coupled to the arterial clamp. The venous line is coupled to the venous clamp. The arterial clamp is closed. The venous clamp is closed. The dialysate chamber of the dialyser is connected to the dialysis circuit as in the dialysis treatment. The rated or nominal or actual permeability value of the dialyser membrane is provided to the control and command unit of the dialyser apparatus, for example by recognition of the dialyser or by a calculation of the permeability made from measured values of ultrafiltration and trans-membrane pressure.

Phase 2 (start of procedure, with removal of the air from the dialysate chamber of the dialyser)—This phase is initiated when the dialysate is ready to be transferred to the dialyser. The priming fluid for the dialysate chamber can be dialysate or isotonic saline solution, prepared on-line by the dialysis apparatus from water and concentrates; in the present embodiment reference is made to dialysate used as priming fluid for the dialysate chamber, without losing in general applicability. In the present embodiment, in which the priming fluid (dialysate) is prepared on-line by the dialysis apparatus, the dialysate is ready for the dialyser if the temperature and the conductivity have values within a predetermined range of acceptability. When the dialysate is ready, the on-off valve V2 on the used dialysate discharge line at the outlet of the dialyser is opened. The by-pass valve is activated to close the by-pass line and to enable flow towards the dialyser. The venous clamp remains closed. The arterial clamp remains closed. The blood pump remains stationery. The suction pump is controlled to maintain a certain pressure in the extracorporeal blood circuit. In particular the suction pump is feedback-controlled by the third pressure sensor at a prefixed pressure. Alternatively, or additionally, the suction pump could be controlled by the arterial pressure sensor and/or the venous pressure sensor. The means for back-filtering are controlled in such a way as to determine a nil or small back-filtration flow across the membrane of the dialysate chamber to the blood chamber. In this phase the dialysate flows through the dialysate chamber from the inlet to the outlet (in particular from the bottom towards the top placing the dialyser in the use position during treatment) in order to fill and tangentially flush or rinse the dialysis chamber. During this phase the air contained in the dialysate chamber is evacuated through the used dialysate discharge line and is thus sent to the drain. In the illustrated embodiment the first pump of the fresh dialysate is controlled at a set flow, for example by the use of a first flow sensor which provides a feedback signal. The second pump of the used dialysate is controlled according to a set flow, for example by use of a second flow sensor providing a feedback signal, in order to obtain a back-filtration flow or an ultrafiltration flow of zero. The second used dialysate pump can be controlled according to the trans-membrane pressure TMP, for example with the aim of obtaining a TMP pressure of practically zero. The trans-membrane pressure is determined in a known way, for example by the use of pressure signals provided by the upstream sensor Pin, by the downstream sensor Pout and by the venous sensor Pven. Other types of control of the first and second pumps (means for back-filtering) are however possible, in which for example the pumps are controlled by a signal indicating the difference of the two flows, or in which both the pumps are controlled according to the trans-membrane pressure TMP, or in which one pump is controlled on the basis of a set value of its rotation speed and the other pump is controlled according to a set value of transmembrane pressure, etc. This phase terminates when an air bubble sensor (of known type and not illustrated) predisposed on the dialysate discharge line no longer detects air bubbles, or after a predetermined time-out. During the following phases the on-off valve V2 of the used dialysate flow to the outlet of the dialyser remains open. The by-pass valve of the dialyser is opened, i.e. brought into the by-pass open position, in which the dialysate by-passes the dialyser and is sent to the drain. Alternatively to opening the by-pass it is possible to control the means for back-filtering and ultrafiltration in such a way that the back-filtration or ultrafiltration flow is zero.

Phase 3 (removal of the air from the blood chamber of the dialyser, from the arterial line and from a part of the venous line)—In this phase the venous clamp remains closed. The arterial clamp is opened. The suction pump Pw is controlled at a set pressure, for example the pressure measured by the third pressure sensor, or the arterial pressure, or the venous pressure. The blood pump is controlled in a reverse direction to the normal direction during treatment (clockwise in FIG. 4) in order to aspirate priming fluid from the bag and transport it from the venous chamber towards the blood chamber of the dialyser and then along the arterial line towards the waste connection port connected to the arterial line, and finally towards the drain. The blood pump is activated at a preset constant speed. During this phase the priming fluid fills a part of the venous line comprised between the venous chamber and the dialyser; further, the priming fluid also fills the blood chamber of the dialyser and the arterial line. At the same time the air contained therein is expelled towards the drain. The aspirated volume produces a corresponding reduction of the volume of the priming bag. This phase terminates after a predetermined volume of priming fluid has been introduced into the extracorporeal circuit, i.e. after, for example, the blood pump (of the positive displacement type) has completed a prefixed number of rotations, or after a predetermined time-out.

Phase 4 (removal of the air from the remaining part of the venous line)—During this phase the part of the extracorporeal circuit between the venous chamber and the patient venous end is filled. During this phase the venous clamp is opened. The arterial clamp is open. The blood pump is stationery. The suction pump is controlled in such a way as to aspirate a flow of priming fluid from the bag. This phase terminates after the air bubble sensor on the venous line no longer detects the presence of air, or after a predetermined time-out starting from the activation of the suction pump, or after a predetermined time-out starting from when the air bubble sensor no longer detects the presence of air. Alternatively the above-described phases 3 and 4 can be performed contemporaneously, keeping the venous clamp open and aspirating a part of the priming fluid from the bag towards the arterial connection port by means of the blood pump, and another part of the priming fluid from the bag towards the venous connection port by means of the suction pump, so that the blood pump flow rate is sufficiently high to generate a flow ration of priming fluid even in the presence of a suction action on the part of the suction pump, so as to determine a first priming flow in the direction which goes from the venous chamber to the patient arterial end (through the blood chamber of the dialyser) and a second priming flow in the direction going from the venous chamber to the patient venous end. In both cases a blood pump (and/or a suction pump) operating cycle can be included, controlled with different velocities at predefined intervals (such as, for example, described herein above), with the aim of facilitating the detachment of the air bubbles from the dialyser membrane, creating intermittent flows with variable velocities able to generate jogs on the membrane.

In enclosed table 1 an example of the operation of the various elements implicated in this priming procedure with priming fluid coming from the bag is reported. In table 1 the duration of each single phase from 1 to 13 is expressed in seconds, the relative values of the blood pump express the blood pump velocity in milliliters per minute (ml/min), OP and CL relate to the arterial and venous clamps and the by-pass and V2 valves and indicate the open configuration (OP) and respectively the closed configuration (CL), the values related to the pump P1 and pump P2 are the set velocity values of the pumps P1 and P2 expressed in milliliters per minute (ml/min), the values relating to the pump Pw are those of the pressure measured by the third pressure sensor, expressed in millimeters of mercury (mmHg), used as set values for feedback control of the pump Pw.

In figures from 5 to 13 some variants of the priming apparatus of the invention are schematically illustrated.

FIG. 5 schematically illustrates the embodiment of FIG. 1. In FIG. 5 the same numbering as in FIG. 1 has been used. The priming apparatus of FIG. 5 comprises two priming fluid discharge ports 61 and 62. Each priming fluid discharge port is connected to a used treatment fluid discharge line by a respective priming fluid discharge line 63 and 64. The two priming fluid discharge lines 63 and 64 unite in a common tract which branches from the used treatment fluid discharge line. Each priming fluid discharge line 63 and 64 is connected to a check valve, respectively 65 and 66, which prevents the flow towards the respective priming fluid discharge port 61 and 62. The used treatment fluid discharge line is connected to an aspiration device (for example a suction pump 40) having an inlet (aspiration or intake) connected to the two priming fluid discharge ports 61 and 62. FIG. 6 shows a variant of the version of FIG. 5 (and the version of FIG. 1) in which, in substitution for (or in addition to) the check valves 65 and 66, on-off valves 103 and 104 are predisposed, which can be, for example, controlled by the control unit of the priming apparatus. FIG. 7 shows a further variant with respect to the version of FIG. 5 (and FIG. 1) in which, in substitution for (or in addition to) the check valves 65 and 66, second means for aspiration are arranged between the first priming fluid discharge port 61 and the second priming fluid discharge port 62. Further, in the variant of FIG. 7, with respect to the version of FIG. 5 (and the version of FIG. 1), the two priming fluid discharge lines 63 and 64 branch off independently from the used treatment fluid discharge line, without having a tract of common line. In particular the second means for aspiration exhibit an inlet (aspiration or intake) connected to one of the two priming fluid discharge ports and an outlet (delivery) connected to the inlet (aspiration or intake) of the suction pump 40. In the illustrated example the second means for aspiration comprise a second suction pump 105. The second suction pump 105 is arranged on the used treatment fluid discharge line. The second means for aspiration are arranged between the two branch points from which the two priming fluid discharge lines 63 and 64 branch off.

FIG. 8 shows a further variant with respect to the version of FIG. 5 (and the version of FIG. 1) in which the priming fluid discharge lines 63 and 64 branch independently from the used fluid discharge line, i.e. without having a common tract of line. In the variant of FIG. 8, in addition to or in substitution for the check valves 65 an 66, other flow control elements can be used, such as in particular two valves, such as for example two on-off valves, or two flow regulators, or two flow chokes or restrictors (fixed or variable, for example, in a controlled way).

FIG. 9 shows a further variant with respect to the version of FIG. 5 (and the version of FIG. 1) in which, in substitution for (or in addition to) check valves 65 and 66, second means for aspiration (for example a second suction pump 105) are arranged in any one of the two priming fluid discharge lines 63 and 64. In the example the second pump 105 is connected to the second priming fluid discharge line 64. In both the version of FIG. 7 and in that of FIG. 9, the first and the second means for aspiration are controlled by the control unit of the priming apparatus in order that during the priming procedure a flow from one to the other of the two priming fluid discharge ports is prevented or, at least, limited.

FIG. 10 illustrates a further variant with respect to the version of FIG. 5 (and the version of FIG. 1), in which, in substitution for (or in addition to) the check valves 65 and 66 and the means for aspiration (pump 40) located on the used treatment fluid line, two distinct means for aspiration are provided, in which first means for aspiration (for example a pump 106) are arranged on the first priming fluid discharge line 63, while second means for aspiration (for example a pump 105) are arranged on the second priming fluid discharge line 64. The priming fluid discharge lines 63 and 64 of FIG. 10 can be configured independently, without a common tract, as in the versions of FIG. 7 or FIG. 8.

FIG. 11 illustrates a further variant with respect to the version of FIG. 5 (and of FIG. 1), in which one of the two priming fluid discharge lines (for example the second priming fluid discharge line 64) is connected to a fluid transport line arranged upstream of a fluid balancing device of an apparatus for extracorporeal blood treatment (for example a hemodialysis apparatus and/or a hemo(dia)filtration apparatus). In FIG. 11, 107 denotes in its entirety a set of elements belonging to the treatment apparatus. The set of elements 107 can comprise, among other things, the fluid balancing device (for example any type of balancing device used in a hemodialysis and/or a hemo(dia)filtration apparatus) and a blood treatment device (for example a hemodialyser and/or a hemo(dia)filter of known type). The set of elements 107 can also comprise one or more (any possible combination) of the treatment apparatus components of FIG. 1. In particular a priming fluid discharge line (for example the first priming fluid discharge line 63) can be made to branch off from the used treatment fluid discharge line, while the other priming fluid discharge line (for example the second line 64) can branch of from the fresh treatment fluid supply line. In the version of FIG. 11 too, two check valves can be arranged in the two priming discharge lines 63 and 64, as in the version of FIG. 5, or other flow control elements controlled or configured in order to prevent or limit reverse flow towards the respective port 61 and 62.

FIG. 12 illustrates a further variant with respect to the version of FIG. 5 (and that of FIG. 1), in which a priming fluid discharge line (for example the first line 63) is connected, as in FIG. 5, to the used treatment fluid discharge line, while the other priming fluid discharge line (for example the second line 64) is connected to a fluid transport line 108 of an extracorporeal blood treatment apparatus, such as for example the apparatus of FIG. 1. The fluid transport line 108 can comprise, for example, a tangential flushing line of an ultrafilter (for example the dialysate ultrafilter downstream of the dialysate preparation device, or the water ultrafilter upstream of the dialysate preparation device), or a vent line of a gas-liquid separation chamber, or a disinfection system line, or a water or dialysate degassing line, or a line of the water or dialysate heating system, or a dialyser by-pass line, or an auxiliary priming line connected to a drain and provided with means for aspirating the priming discharge fluid. The fluid transport line 108 is connected to a flow control element, denoted by 109 in FIG. 12. The flow control element 109 is arranged on the fluid transport line 108 downstream of the branch point from which the priming fluid discharge line 64 branches off, where downstream is taken to mean with reference to a discharge flow direction of the excess fluid during the priming procedure. The flow control element 109 can comprise, for example, one or more valves (on-off, check, flow distribution, flow limitation, etc.) and/or a flow rate regulator or a pressure regulator (a suction pump, a controlled variable choke or restrictor, a fixed choke or restrictor, a pressure regulator etc.) or a combination of two or more of the above-mentioned elements.

FIG. 13 illustrates a particular case of the version of FIG. 12, in which the fluid transport line 108 branches from the used treatment fluid discharge line. In the specific case the fluid transport line 108 is connected to the inlet (aspiration or intake) of the means for aspiration (for example the suction pump 40) predisposed on the used treatment fluid discharge line. Both in the version of FIG. 12 and in that of FIG. 13, each priming fluid discharge line 63 and 64 can be provided with a respective flow control element, such as for example one or more valves, such as in particular a check valve, or an on-off valve commanded by the control unit, etc. Other embodiments can be provided in which both priming fluid discharge lines 63 and 64 are connected in branching relation to a tract of the fresh liquid (water, dialysate, isotonic saline, or other treatment liquid) supply line, or to any tract of a fluid transport line of the hydraulic circuit of the machine of FIG. 1, for example a tract arranged upstream of the blood treatment device (dialyser 33). Both priming fluid discharge lines 63 and 64 can be connected in branching relation to the fluid transport line 108 with the flow control element 109 arranged therebetween.

The above-described priming procedures with reference to figures from 2 to 4 can be performed in relation to each of the apparatus of figures from 5 to 13. To this end each of the apparatus of figures from 5 to 13 is operatively associated to an extracorporeal circuit, for example any of the extracorporeal circuits described with reference to figures from 2 to 4.

In other embodiments (not illustrated), instead of the dialyser of figures from 2 to 4 a hemodiafilter is provided, or a hemofilter. In these cases the priming apparatus is applied to a hemodiafiltration apparatus and, respectively, a hemofiltration apparatus, and exhibits the same characteristics as described for the embodiments of figures from 1 to 4. In all of these cases too it is possible to operatively associate any one of the priming apparatus described with reference to figures from 5 to 13.

With reference to all the embodiments first mentioned, the priming fluid source can comprise, in addition to or in substitution for the previously-described sources, a supply line of an isotonic saline fluid (for example a substitution fluid) prepared by the machine for hemo(dia)filtration 1, in which the supply line has an inlet end connected to the device 20 for on-line preparation of a dialysis liquid with water and concentrates, and one or two outlet ends connected to the extracorporeal blood circuit (to the venous line and/or the arterial line). This supply line can comprise an ultrafilter for ultrafiltering the liquid preparation in such a way as to make it suitable for injection into a blood circuit. This supply line can comprise, for example, the substitution liquid supply line 75.

The first and second discharge ports are non-disposable, where disposable is taken to mean an element destined to be used for a limited number of times, for example for a single use, or for a use of not more than a predefined number of times or work cycles, or for a use not above a predefined working time, while a non-disposable element is taken to mean an element destined to be used for an indefinite or in any case large number of time or work cycles (for example at least ten, or a hundred, or a thousand, or five thousand priming cycles) or for an equivalent working time of the priming apparatus (for example two priming hours, or twenty hours, or two hundred hours, or a thousand priming hours). The length of use of the non-disposable element can be defined instead of in terms of priming cycles or priming times, on the basis of the number (high) of treatments before, during or after which the element is used, or on the basis of the work time of the extracorporeal blood treatment apparatus to which the priming apparatus is associated during which the non-disposable element remains operative. Obviously, as with any component of an apparatus, the priming waste fluid discharge ports can require removal, for example for extra cleaning or for unforeseen replacement due to faults or malfunctioning, or for programmed replacement due to wear, and so on. In any case the discharge ports are components that are configured such as to remain associated to the priming apparatus permanently, under normal conditions, for at least ten, or a hundred, or a thousand, or five thousand priming cycles, or indeed for the whole working life of the entire apparatus. In other words, both the first and the second discharge ports are connected to the casing of the priming apparatus, i.e. to the extracorporeal blood treatment apparatus, in a non-removable way, or permanently. This means, in substance, that the discharge ports comprise two openings 110 predisposed on a panel (for example frontal) of the apparatus casing, in an easily-accessible position for an operator (see FIGS. 14 and 15). In other words, each of the apparatuses above described comprises a casing defining internally thereof a containing space. In each of the above described apparatuses, the two priming fluid discharge ports each comprise an opening 110 made on a panel of the casing. The treatment fluid circuit of each described apparatus is at least in part arranged internally of this containing space. In particular the first and second priming fluid discharge lines are arranged internally of said containing space.

In each of the above described apparatuses, the first discharge port 61 is provided with a first hatch 111 which can assume a closed position and an open position of the first discharge port (see FIGS. 14 and 15). The first discharge port 61 is also provided with a first sensor (not illustrated) configured to provide a signal indicating at least a position of the first hatch 111. The second discharge port 62 is provided with a second hatch 112 which can assume a closed position and an open position of the second discharge port 62 (see FIGS. 14 and 15). The second discharge port 62 is further provided with a second sensor (not illustrated) configured to provide a signal indicating at least a position of the second hatch 112. The two hatches 111 and 112 can each comprise a rotating coupling with the casing of the apparatus, such as for example a hinge or a sliding coupling. The two sensors can each comprise a sensor of position of the respective hatch 111 and 112, such as for example a Hall sensor. Each sensor can be configured to send a signal to the control unit only when the relative hatch is in the closed position. The control unit is programmed to perform the priming method according to a signal received from the first sensor and a signal received from the second sensor. In particular the control unit is programmed not to consent to a performing of the priming method if at least one of the hatches 111 and 112 is detected to be in the closed position.

An embodiment can be provided in which the first hatch and the second hatch are integrated in a single hatch able to close both the first and the second discharge ports of the priming waste. In this case the two discharge ports are arranged side-by-side and are operatively associated to the same closure hatch. In this case it is possible operatively to associate a single position sensor (e.g. a Hall sensor) of the hatch to the single hatch.

LEGEND 1. hemodiafiltration apparatus
2. water inlet
3. inlet pressure sensor
4. inlet pressure regulator
5. inlet on-off valve
6. ultrafilter for water at the inlet
7. first heat exchanger
8. second heat exchanger
9. flow sensor or presence of flow sensor at the inlet of the heating and degassing circuit
10. heater
11. temperature sensor in the heating and degassing circuit 12. degassing choke or restrictor
13. by-pass valve of the degassing choke or restrictor
14. pressure sensor of the degassing choke or restrictor
15. degassing pump
16. first gas-liquid separator in the heating and degassing circuit
17. first degassing valve
18. check valve for the heating and degassing circuit
19. pressure regulator at the outlet of the heating and degassing circuit
20. device for on-line preparation of a dialysate with water and concentrates
21. pump for moving the fresh dialysate
22. second gas-liquid separator for the fresh dialysate
23. second degassing valve
24. sensor system for measuring some parameters (in particular temperature, conductivity, and pH) of the fresh dialysate
25. protection system of redundant fluid balance in the control system
26. fluid balance control system
27. pressure sensor at the dialysate ultrafilter inlet
28. first by-pass valve for the by-pass of the dialysate ultrafilter
29. dialysate ultrafilter
30. connection for a disposable line for substitution liquid
31. second by-pass valve for the by-pass of the dialysate ultrafilter
32. pressure sensor at the dialyser inlet
33. dialyser
34. on-off valve at the dialyser outlet
35. pressure sensor at the dialyser outlet
36. pump for moving the used dialysate
37. third gas-liquid separator for the used dialysate
38. third degassing valve
39. sensor system for measuring some parameters (in particular temperature, conductivity, pressure and presence of blood loss) of the used dialysate
40. suction pump for stabilization of the pressure downstream of the fluid balance control system
41. normally open on-off valve at the outlet
42. pressure sensor at the outlet
43. check valve at the outlet
44. outlet end connected to a drain
45. flushing line of the water ultrafilter
46. choke or restrictor on the flushing line
47. on-off valve on the flushing line
48. vent circuit connected to the vents of the various gas-liquid separators
49. choke or restrictor connected to the vents of the various gas-liquid separators
50. check valve operating on a tract of line in common with the flushing line and the vent circuit
51. recirculating circuit for complete thermal or chemical disinfection of the circuit
52. chemical disinfectant source including the means for supplying the disinfectant
53. first on-off valve for enabling recirculation during the thermal or chemical disinfection
54. pair of connectors for the by-pass of the dialyser during thermal or chemical disinfection
55. flow sensor in the dialyser by-pass
56. second on-off valve for enabling recirculation during thermal or chemical disinfection
57. first on-off valve for enabling supply of disinfectant to the first port of the priming fluid discharge
58. second on-off valve for enabling supply of disinfectant to the second port of the priming fluid discharge
59. first branch for disinfection of the first port of the priming fluid discharge
60. second branch for disinfection of the first port of the priming fluid discharge
61. first discharge port of the priming fluid
62. first discharge port of the priming fluid
63. first discharge line of the priming fluid
64. second discharge line of the priming fluid
65. first check valve
66. second check valve
67. line joining the first and the second priming fluid discharge lines with the used dialysate line
68. connection line with the outside environment upstream of the heating and degassing circuit
69. on-off valve of the connection line with the outside environment
70. air filter
71. first by-pass line (dialysate ultrafilter by-pass)
72. second by-pass line (dialyser by-pass)
73. flushing line of the dialysate ultrafilter
74. on-off valve of the dialysate ultrafilter flushing line
75. substitution liquid supply line
76. substitution liquid pump
77. substitution liquid ultrafilter
78. substitution liquid ultrafilter vent system
79. arterial line
80. blood pump
81. arterial chamber
82. service line of arterial chamber
83. arterial clamp
84. access site in the arterial line
85. anticoagulant supply line
86. anticoagulant source
87. venous line
88. venous chamber
89. service line of the venous chamber
90. venous clamp
91. venous line access site
92. air bubble sensor
93. blood presence sensor, or patient sensor
94. hemoglobin sensor, or hematocrit, or blood volume sensor
95. third pressure sensor upstream of the suction pump 40
96. arterial pressure measuring device
97. venous pressure measuring device
98. priming fluid container (bag)
99. removable connection between the priming fluid container and the extracorporeal blood circuit
100. second arterial blood storage chamber for single needle extracorporeal treatment
101. second blood pump (venous) for single needle extracorporeal treatment
102. second venous blood storage chamber for single needle extracorporeal treatment
103. first on-off valve commanded by the control unit of the priming apparatus
104. second on-off valve commanded by the control unit of the priming apparatus
105. second suction pump or suction pump operating between the first and the second priming discharge line
106. third suction pump or suction pump operating between the first and the second priming discharge line
107. system of elements belonging to the hydraulic circuit of the extracorporeal blood treatment apparatus including the fluid balancing device and the blood treatment device (exchanger or dialysis filter membrane)
108. fluid transport line
109. flow control element
110. openings defining the two priming fluid discharge ports 61 and 62
111. first hatch
112. second hatch

TABLE 1

| ENCLOSURE—(Priming with bag supply) | | | | | | | | | | | | | |
|---|---|---|---|---|---|---|---|---|---|---|---|---|---|
|  | 1 | 2 | 3 | 4 | 5 | 6 | 7 | 8 | 9 | 10 | 11 | 12 | 13 |
| Time | 2' | 3'20" | 4' | 4'5" | 4'20" | 5' | 5'20" | 6' | 6'20" | 7' | 7'7" | 7'37" | 7'42" |
| Duration | 120 | 80 | 40 | 5 | 15 | 40 | 20 | 40 | 20 | 40 | 7 | 30 | 5 |
| Blood pump | 0 | 150 | 0 | 200 | 400 | 200 | 400 | 200 | 400 | 200 | 150 | 50 | 0 |
| Arterial clamp | CL | OP | OP | OP | OP | OP | OP | OP | OP | OP | OP | OP | CL |
| Venous clamp | CL | CL | OP | OP | OP | OP | OP | OP | OP | OP | OP | OP | CL |
| Bypass valve | OP | OP | CL | CL | CL | CL | CL | CL | CL | CL | CL | CL | OP |
| Valve V2 | CL | CL | OP | OP | OP | OP | OP | OP | OP | OP | OP | OP | CL |
| Pump P1 | 400 | 400 | 400 | 400 | 400 | 400 | 400 | 400 | 400 | 400 | 400 | 400 | 400 |
| Pump P2 | 400 | 400 | 400 | 400 | 400 | 450 | 400 | 450 | 400 | 450 | 400 | 400 | 400 |
| Pump Pw | 0 | 0 | 0 | −350 | −450 | −100 | −200 | −100 | −200 | −100 | −300 | −200 | 0 |

The invention claimed is:

1. An extracorporeal blood treatment apparatus comprising:
   a casing internally defining a containing space;
   a treatment fluid circuit which is arranged internally of the containing space, the treatment fluid circuit comprising:
   a fresh treatment fluid supply line which is configured to connect a treatment fluid source with a fluid chamber of a blood treatment device of a type having a semipermeable membrane; and
   a used treatment fluid discharge line which is configured to connect the fluid chamber with a drain;
   a waste priming fluid discharge apparatus comprising:
   a first priming fluid discharge port which comprises a respective first opening obtained on said casing;
   a first priming fluid discharge line which connects the first priming fluid discharge port with the used treatment fluid discharge line, the first priming fluid discharge line having at least a first tract thereof arranged internally of the containing space, wherein the first priming fluid discharge line includes a first check valve which is configured to block flow towards the first priming fluid discharge port;
   a second priming fluid discharge port which comprises a respective second opening obtained on said casing; and
   a second priming fluid discharge line which connects the second priming fluid discharge port with the used treatment fluid waste line, the second priming fluid discharge line having at least a second tract arranged internally of the containing space, the second tract being distinct from the first tract, wherein the second priming fluid discharge line includes a second check valve which is configured to block flow towards the second priming fluid discharge port; and
   the apparatus being further configured to hold an extracorporeal blood circuit comprising:
   a blood chamber of said blood treatment device in which the semipermeable membrane separates the blood chamber from the fluid chamber;
   an arterial blood line having a first arterial end connected to the blood chamber and a second arterial end;
   a venous blood line having a first venous end connected to the blood chamber and a second venous end;
   wherein the first priming fluid discharge port is configured to removably receive one of said second arterial end and said second venous end, and wherein the second priming fluid discharge port is configured to removably receive the other of said second arterial end and said second venous end.

2. Apparatus according to claim 1, further comprising means configured for filling the extracorporeal blood circuit with a priming fluid when said second venous end and said second arterial end are connected to said first and second priming fluid discharge ports.

3. Apparatus according to claim 2, further comprising means configured for discharging said priming fluid from the extracorporeal blood circuit through the first priming fluid discharge port and/or through the second priming fluid discharge port.

4. Apparatus according to claim 3 further comprising a control unit connected to the means for filling and the means for discharging, the control unit being programmed to perform a priming method comprising steps of:
   activating the means for filling and filling the extracorporeal blood circuit with a priming fluid; and
   activating the means for discharging and discharging a fluid from the extracorporeal blood circuit through the first priming fluid discharge port and/or through the second priming fluid discharge port.

5. Apparatus according to claim 1 wherein the first and the second priming fluid discharge ports are arranged in a zone of the apparatus which is accessible from the outside of said casing.

6. Apparatus according to claim 1 wherein the first and the second priming fluid discharge ports are configured for sealedly and removably connecting with the second arterial end and the second venous end of the extracorporeal blood circuit.

7. Apparatus according to claim 1 wherein the first and second priming fluid discharge ports each comprise an opening made on a panel of the casing.

8. Apparatus according to claim 1 wherein the first priming fluid discharge port has a first closure element which is configured to take at least a closed position and an open position of the first priming fluid discharge port, the first priming fluid discharge port further having a first sensor configured for providing a signal indicating at least one of said positions taken by the first closure element.

9. Apparatus according to claim 8 wherein the second priming fluid discharge port has a second closure element which is configured to take at least a closed position and an open position of the second priming fluid discharge port, the second priming fluid discharge port further having a second sensor configured for providing a signal indicating at least one of said positions taken by the second closure element.

10. Apparatus according to claim 9 further comprising:
means configured for filling the extracorporeal blood circuit with a priming fluid when said second venous end and said second arterial end are connected to said first and second priming fluid discharge ports;
means for discharging a waste fluid from the extracorporeal blood circuit through the first priming fluid discharge port and/or through the second priming fluid discharge port, the discharge fluid comprising air and/or excess priming fluid; and
a control unit connected to the means for filling and to the means for discharging, the control unit being further connected to the first and the second sensors, the control unit being programmed to perform a priming method comprising steps of:
filling the extracorporeal blood circuit with a priming fluid; and
discharging a waste fluid from the extracorporeal blood circuit through the first discharge port and/or through the second discharge port, the waste fluid comprising air and/or excess priming fluid.

11. The apparatus of claim 10, wherein the control unit is programmed to perform the priming method based on a signal received from the first sensor and/or a signal received from the second sensor.

12. The apparatus of claim 10 wherein the control unit is programmed to perform the priming method according to a signal received from the first sensor and a signal received from the second sensor.

13. Apparatus according to claim 12, wherein the control unit is programmed not to consent to a performing of the priming method if at least one of the first and second closure elements is detected to be in closed position.

14. Apparatus according to claim 9, wherein the first closure element and the second closure element are integrated in a single closure element, and wherein the first sensor and the second sensor are integrated in a single sensor.

15. Apparatus according to claim 9 wherein the first and second closure elements each comprise a coupling with the casing of the apparatus selected in the group of a hinge coupling and a sliding coupling.

16. Apparatus according to claim 9 wherein each of the first and second sensors comprises a sensor of position of the respective first and second closure element.

17. Apparatus according to claim 9 wherein each of the first and second sensors is configured to a respective signal to the control unit only when the relative first or second closure element is in the closed position.

18. Apparatus according to claim 16, wherein each of the first and second sensors comprises a Hall sensor.

19. Apparatus according to claim 10 further wherein the means for filling comprises at least one blood pump configured to couple one of the arterial and the venous blood lines; the control unit being connected to the blood pump and being configured to activate the blood pump for causing filling the extracorporeal blood circuit with priming liquid.

20. Apparatus according to claim 10 wherein the means for discharging includes means connected to the fluid circuit for aspirating fluid from the first discharge port and/or from the second discharge port, wherein the control unit is configured for activating the means for discharging and causing discharging fluid from the extracorporeal blood circuit.

21. Apparatus according to claim 10 wherein the means for filling comprises means configured for transferring a fluid from the fluid chamber to the blood chamber through the semipermeable membrane.

22. Apparatus according to claim 10 wherein the means for filling comprises a container of priming fluid connected to the extracorporeal blood circuit, and means for transferring the priming fluid from the container to the extracorporeal blood circuit.

23. Apparatus according to claim 10 comprising an arterial clamp and a venous clamp connected to the arterial line and, respectively, to the venous line and the means for discharging includes means connected to the fluid circuit for aspirating fluid from the first priming fluid discharge port; the control unit being connected to the venous clamp and to the means for aspirating from the first priming fluid discharge port, said control unit being configured for closing the venous clamp and activating the means for aspirating from the first priming fluid discharge port.

24. Apparatus according to claim 23 wherein the means for discharging comprises means connected to the fluid circuit for aspirating fluid from the second priming fluid discharge port; the control unit being connected to the arterial clamp and to the means for aspirating from the second priming fluid discharge port, the control unit being configured for closing the arterial clamp and activating the means for aspirating fluid from the second priming fluid discharge port.

* * * * *